United States Patent
Yu et al.

(10) Patent No.: US 7,048,920 B2
(45) Date of Patent: May 23, 2006

(54) RECOMBINANT ONCOLYTIC ADENOVIRUS FOR HUMAN MELANOMA

(75) Inventors: De Chao Yu, Foster City, CA (US); Yuanhao Li, Palo Alto, CA (US)

(73) Assignee: Cell Genesys, Inc., South San Francisco, CA (US)

( * ) Notice: Subject to any disclaimer, the term of this patent is extended or adjusted under 35 U.S.C. 154(b) by 158 days.

(21) Appl. No.: 10/053,886

(22) Filed: Jan. 15, 2002

(65) Prior Publication Data

US 2003/0039633 A1    Feb. 27, 2003

Related U.S. Application Data

(63) Continuation-in-part of application No. 09/814,357, filed on Mar. 21, 2001, now Pat. No. 6,911,200, and a continuation-in-part of application No. 09/814,351, filed on Mar. 21, 2001, now Pat. No. 6,692,736.

(60) Provisional application No. 60/192,015, filed on Mar. 24, 2000, provisional application No. 60/192,156, filed on Mar. 24, 2000.

(51) Int. Cl.
*A01N 63/00* (2006.01)
*A61K 48/00* (2006.01)

(52) U.S. Cl. .................. 424/93.2; 435/455; 435/456; 435/320.1

(58) Field of Classification Search .............. 514/44; 435/320.1, 455, 456; 424/93.21, 93.2
See application file for complete search history.

(56) References Cited

U.S. PATENT DOCUMENTS

| | | | |
|---|---|---|---|
| 5,679,511 A * | 10/1997 | Kwon ........................... | 435/6 |
| 5,698,443 A | 12/1997 | Henderson et al. ....... | 435/720.1 |
| 5,747,469 A | 5/1998 | Roth et al. ..................... | 514/44 |
| 5,776,743 A | 7/1998 | Frisch ...................... | 435/172.3 |
| 5,801,029 A | 9/1998 | McCormick ............. | 435/172.3 |
| 5,824,543 A | 10/1998 | Sun .......................... | 435/320.1 |
| 5,846,945 A | 12/1998 | McCormick ................. | 514/44 |
| 5,998,205 A | 12/1999 | Hallenbeck et al. ......... | 435/325 |
| 6,001,646 A | 12/1999 | Sun .......................... | 435/320.1 |
| 6,692,736 B1 * | 2/2004 | Yu et al. ..................... | 424/93.2 |
| 2003/0026789 A1 * | 2/2003 | Gregory et al. | |
| 2003/0152553 A1 * | 8/2003 | Little et al. | |

FOREIGN PATENT DOCUMENTS

| | | |
|---|---|---|
| WO | WO 95/19434 | 7/1995 |
| WO | WO 96/17053 | 6/1996 |
| WO | WO 97/01358 | 1/1997 |
| WO | WO 97/10007 | 3/1997 |
| WO | WO 98/29555 | 7/1998 |
| WO | WO 9829555 | 7/1998 |
| WO | WO 98/35554 | 8/1998 |
| WO | WO 98/37189 | 8/1998 |
| WO | WO 09/39465 | 9/1998 |
| WO | WO 98/39464 | 9/1998 |
| WO | WO 98/39466 | 9/1998 |
| WO | WO 98/39467 | 9/1998 |
| WO | WO 99/06576 | 2/1999 |
| WO | WO 99/25860 | 5/1999 |
| WO | WO 99/59604 | 11/1999 |
| WO | WO 9959604 | 11/1999 |
| WO | WO 00/15820 | 3/2000 |
| WO | WO 00/39319 | 7/2000 |
| WO | WO 9835554 | 4/2003 |

OTHER PUBLICATIONS

Duque et al., Cancer Gene Therapy, vol. 6, pp. 554-563, 1999.*
Alemany, et al. *Nat. Biotechnol.*, (2000) vol. 18: 723-727.
Hallenbeck, et al., *Hum. Gene Ther.* (1999) vol. 10: 1721-1733.
Herman, Ronald C., "Alternatives for the initiation of translation", Trends in Biochemical Sciences, vol. 14, No. 6, Jun. 1989.
Jackson, Richard J. et al., "Internal initiation of translation in eukaryotes: The picornavirus paradigm and beyond", RNA 1, pp. 985-1000, 1995.
Lin, Jun-Hsiang et al., "A tissue-specific promoter that can drive a foreign gene to express in the suprabasal urothelial cells of transgenic mice", Proc. Natnl. Acad. Sci. USA, vol. 92, pp. 679-683, Jan. 1995.
Yu, et al. *Cancer Res.*, (1999) vol. 59: 1498-1504.

* cited by examiner

*Primary Examiner*—Joseph Woitach
*Assistant Examiner*—Brian Whiteman
(74) *Attorney, Agent, or Firm*—DLA Piper Rudnick; Gray Cary US LLP

(57) ABSTRACT

The invention provides melanoma cell specific adenovirus vectors, which preferentially replicate in melanoma cells.

19 Claims, 5 Drawing Sheets

SEQUENCE LISTING

<160> NUMBER OF SEQ ID NOS: 21

<210> SEQ ID NO 1
<211> LENGTH: 546
<212> TYPE: DNA
<213> ORGANISM: H. sapiens

<400> SEQUENCE: 1

```
ccggttgaaa atgataagtt gaattctgtc ttcgagaaca tagaaaagaa ttatgaaatg      60
ccaacatgtg gttacaagta atgcagaccc aaggctcccc agggacaaga agtcttgtgt     120
taactctttg tggctctgaa agaaagagag agagaaaaga ttaagcctcc ttgtggagat     180
catgtgatga cttcctgatt ccagccagag cgagcatttc catggaaact tctcttcctc     240
ttcactcgag attactaacc ttattgttaa tattctaacc ataagaatta aactattaat     300
ggtgaataga gttttcact ttaacatagg cctatcccac tggtgggata cgagccaatt      360
cgaaagaaaa agtcagtcat gtgcttttca gaggatgaaa gcttaagata aagactaaaa     420
gtgtttgatg ctggaggtgg gagtggtatt ataggtct cagccaagac atgtgataat       480
cactgtagta gtagctggaa agagaaatct gtgactccaa ttagccagtt cctgcagacc     540
ttgtga                                                                546
```

<210> SEQ ID NO 2
<211> LENGTH: 28
<212> TYPE: DNA
<213> ORGANISM: M. musculus

<400> SEQUENCE: 2

```
cggccgcaag gtcatagttc ctgccagc                                         28
```

<210> SEQ ID NO 3
<211> LENGTH: 29
<212> TYPE: DNA
<213> ORGANISM: M. musculus

<400> SEQUENCE: 3

```
tactcgagta ttgtggtttg ccaggaccc                                        29
```

<210> SEQ ID NO 4
<211> LENGTH: 219
<212> TYPE: DNA
<213> ORGANISM: M. musculus
<220> FEATURE:
<221> NAME/KEY: misc_feature
<222> LOCATION: (1)...(6)
<223> OTHER INFORMATION: EagI restriction site
<220> FEATURE:
<221> NAME/KEY: misc_feature
<222> LOCATION: (214)...(219)
<223> OTHER INFORMATION: XhoI restriction site

<400> SEQUENCE: 4

```
cggccgcaag gtcatagttc ctgccagctg actttgtcaa gacagtgatg tctgtgttcc      60
agcagttgtt ctgagtatcc ttttcattat ccactgtcct ttcttcttaa attccacccc     120
caacattgta aatagcttct ttcttaaact ctgttcaaag aaccagcttg agtgtgtcag     180
ctgcttctgc tgggtcctg gcaaaccaca atactcgag                              219
```

<210> SEQ ID NO 5
<211> LENGTH: 25
<212> TYPE: DNA

```
<213> ORGANISM: M. musculus

<400> SEQUENCE: 5
cggccgtgtc acagacttct tttcc                                            25

<210> SEQ ID NO 6
<211> LENGTH: 29
<212> TYPE: DNA
<213> ORGANISM: M. musculus

<400> SEQUENCE: 6
tactcgagga atctagatgt ttcatgacc                                        29

<210> SEQ ID NO 7
<211> LENGTH: 320
<212> TYPE: DNA
<213> ORGANISM: M. musculus
<220> FEATURE:
<221> NAME/KEY: misc_feature
<222> LOCATION: (1)...(6)
<223> OTHER INFORMATION: XhoI restriction site
<220> FEATURE:
<221> NAME/KEY: misc_feature
<222> LOCATION: (315)...(320)
<223> OTHER INFORMATION: EagI restriction site

<400> SEQUENCE: 7
ctcgaggaat ctagatgttt catgaccttt attcataaga gatgatgtat tcttgatact       60
acttctcatt tgcaaattcc aattattatt aatttcatat caattagaat aatatatctt     120
ccttcaattt agttacctca ctatgggcta tgtacaaact ccaagaaaaa gttagtcatg     180
tgctttgcag aagataaaag cttagtgtaa acaggctga gagtatttga tgtaagaagg      240
ggagtggtta tataggtctt agccaaaaca tgtgatagtc actccagggg ttgctggaaa    300
agaagtctgt gacacggccg                                                320

<210> SEQ ID NO 8
<211> LENGTH: 32
<212> TYPE: DNA
<213> ORGANISM: M. musculus

<400> SEQUENCE: 8
aaataccggt caaggtcata gttcctgcca gc                                    32

<210> SEQ ID NO 9
<211> LENGTH: 32
<212> TYPE: DNA
<213> ORGANISM: M. musculus

<400> SEQUENCE: 9
aaataccggt gagtgtcaca gacttctttt cc                                    32

<210> SEQ ID NO 10
<211> LENGTH: 28
<212> TYPE: DNA
<213> ORGANISM: M. musculus

<400> SEQUENCE: 10
actcgagaag gtcatagttc ctgccagc                                         28

<210> SEQ ID NO 11
<211> LENGTH: 28
<212> TYPE: DNA
<213> ORGANISM: M. musculus
```

```
<400> SEQUENCE: 11
actcgagtat tgtggtttgc caggaccc                                        28

<210> SEQ ID NO 12
<211> LENGTH: 35
<212> TYPE: DNA
<213> ORGANISM: H. sapiens

<400> SEQUENCE: 12
aaccggttga aaatgataag ttgaattctg tcttc                                35

<210> SEQ ID NO 13
<211> LENGTH: 31
<212> TYPE: DNA
<213> ORGANISM: H. sapiens

<400> SEQUENCE: 13
actcgagtga agaggaagag aagtttccat g                                    31

<210> SEQ ID NO 14
<211> LENGTH: 37
<212> TYPE: DNA
<213> ORGANISM: H. sapiens

<400> SEQUENCE: 14
actcgagatt actaacctta ttgttaatat tctaacc                              37

<210> SEQ ID NO 15
<211> LENGTH: 29
<212> TYPE: DNA
<213> ORGANISM: H. sapiens

<400> SEQUENCE: 15
aaccggtcac aaggtctgca ggaactggc                                       29

<210> SEQ ID NO 16
<211> LENGTH: 552
<212> TYPE: DNA
<213> ORGANISM: H. sapiens
<220> FEATURE:
<221> NAME/KEY: misc_feature
<222> LOCATION: (1)...(6)
<223> OTHER INFORMATION: AgeI restriction site
<220> FEATURE:
<221> NAME/KEY: misc_feature
<222> LOCATION: (547)...(552)
<223> OTHER INFORMATION: AgeI restriction site

<400> SEQUENCE: 16
accggttgaa aatgataagt tgaattctgt cttcgagaac atagaaaaga attatgaaat      60
gccaacatgt ggttacaagt aatgcagacc caaggctccc cagggacaag aagtcttgtg    120
ttaactcttt gtggctctga agaaagaga gagagaaaag attaagcctc cttgtggaga     180
tcatgtgatg acttcctgat tccagccaga gcgagcattt ccatgaaaac ttctcttcct    240
cttcactcga gattactaac cttattgtta atattctaac cataagaatt aaactattaa    300
tggtgaatag agttttttcac tttaacatag gcctatccca ctggtgggat acgagccaat   360
tcgaaagaaa aagtcagtca tgtgcttttc agaggatgaa agcttaagat aaagactaaa    420
agtgtttgat gctggaggtg ggagtggtat tatataggtc tcagccaaga catgtgataa    480
tcactgtagt agtagctgga aagagaaatc tgtgactcca attagccagt tcctgcagac    540
```

```
cttgtgaccg gt                                                              552
```

<210> SEQ ID NO 17
<211> LENGTH: 34
<212> TYPE: DNA
<213> ORGANISM: H. sapiens

<400> SEQUENCE: 17

```
aaataccggt caaaagtaat tgtggtgtcg gacc                                       34
```

<210> SEQ ID NO 18
<211> LENGTH: 31
<212> TYPE: DNA
<213> ORGANISM: H. sapiens

<400> SEQUENCE: 18

```
aaataccggt agtcctctgt ctgctggctg g                                          31
```

<210> SEQ ID NO 19
<211> LENGTH: 374
<212> TYPE: DNA
<213> ORGANISM: H. sapiens
<220> FEATURE:
<221> NAME/KEY: misc_feature
<222> LOCATION: (5)...(10)
<223> OTHER INFORMATION: AgeI restriction site
<220> FEATURE:
<221> NAME/KEY: misc_feature
<222> LOCATION: (364)...(370)
<223> OTHER INFORMATION: AgeI restriction site

<400> SEQUENCE: 19

```
aaataccggt caaaagtaat tgtggtgtcg gaccatgaat tttaaatcat tataactagg           60
ctcatgtcat attttatgtg acatggcaat cctatggagg agggaccaac atttaaaata          120
aatggcttcc ctaggataga gcactgggac tggggaaaa cagaggccac agtcagctgt          180
gacttttga aggaaggaat aaagttggtt tctttcatgc caatttagca attacgaacg          240
accccgtcag aaatctaaac ccgtgactat catgggactc aaaaccagga aaaaaataa          300
gtcaaaacga ttaagagcca gagaagcatc ttcatacacg cggccagcca gcagacagag          360
gactaccggt attt                                                           374
```

<210> SEQ ID NO 20
<211> LENGTH: 30
<212> TYPE: DNA
<213> ORGANISM: H. sapiens

<400> SEQUENCE: 20

```
cggccgcaaa agtaattgtg gtgtcggacc                                            30
```

<210> SEQ ID NO 21
<211> LENGTH: 29
<212> TYPE: DNA
<213> ORGANISM: H. sapiens

<400> SEQUENCE: 21

```
attctagaag tcctctgtct gctggctgg                                             29
```

RECOMBINANT ONCOLYTIC ADENOVIRUS FOR HUMAN MELANOMA

CROSS-REFERENCE TO RELATED APPLICATIONS

This application in a continuation-in-part of U.S. patent application Ser. No. 09/814,357 U.S. Pat. No. 6,911,200, filed Mar. 21, 2001 which claims the benefit of U.S. Provisional Patent Application No. 60/192,015 filed Mar. 24, 2000; and a continuation-in-part of U.S. patent application Ser. No. 09/814,351 U.S. Pat. No. 6,692,736, filed Mar. 21, 2001 which claims the benefit of U.S. Provisional Patent Application No. 60/192,156 filed Mar. 24, 2000.

TECHNICAL FIELD

The technical field of the invention is methods of using adenoviral vectors for the suppression of melanoma.

BACKGROUND OF THE INVENTION

Neoplasia, also known as cancer, is the second most common cause of death in the United States. While the survival rates for individuals with cancer have increased considerably in the last few decades, survival of the disease is far from assured. Cancer is a catch-all term for over 100 different diseases, each of which are each fundamentally characterized by the unchecked proliferation of cells. Individual cancer cells are also able to break off from the main tumor, or metastasize, creating additional tumors in other regions of the body.

Melanoma is a very serious form of cancer. Recently, the number of new melanomas diagnosed has been increasing. The American Cancer Society estimates that about 51,400 new melanomas will be diagnosed in the United States during 2001, and about 7,800 deaths will be attributed to the disease.

Melanoma is a malignant tumor of melanocytes. Although most melanomas arise in the skin, they also may arise from mucosal surfaces or at other sites to which neural crest cells migrate. Melanoma occurs predominantly in adults, and more than half of the cases arise in apparently normal areas of the skin. Prognosis is affected by clinical and histological factors and by anatomic location of the lesion. Thickness and/or level of invasion of the melanoma, mitotic index, tumor infiltrating lymphocytes, and ulceration or bleeding at the primary site affect the prognosis. Clinical staging is based on whether the tumor has spread to regional lymph nodes or distant sites. Melanoma can spread by local extension (through lymphatics) and/or by hematogenous routes to distant sites. Any organ may be involved by metastases, but lungs and liver are common sites.

Melanomas that have not spread beyond the site at which they developed are highly curable. Most of these are thin lesions that have not invaded beyond the papillary dermis. The treatment of localized melanoma is surgical excision with margins proportional to the microstage of the primary lesion. Some melanomas that have spread to regional lymph nodes may be curable with wide excision of the primary tumor and removal of the involved regional lymph nodes. Adjuvant chemotherapy has not been shown to increase survival. Melanoma that has spread to distant sites is generally not curable with standard therapy, although long-term survival is occasionally achieved by resection of metastasis. Such patients are appropriately considered candidates for clinical trials exploring new forms of therapy.

Recently, immunotherapies by using melanoma-specific antigens or epitopes have been documented, with immunogenic antigens identified including human tyrosinase, TRP-1 (tyrosinase related protein 1), TRP-2, a group of enzymes involved in melanin biosynthetic pathway, MART-1/melan-A (Melanoma Antigen Recognized by cytolytic T cells-1), MAGE-1, BAGE-1 etc. A number of these human antigens have corresponding non-human mammalian counterparts which share significant homology in their coding sequences and TREs and which may find utility in the practice of the present invention.

Several viruses have recently come forth as both vehicles for gene therapy and as candidate anticancer agents. Among them adenovirus, a mildly pathogenic human virus that propagates prolifically in epithelial cells, the origin of many human cancers. Adenovirus has emerged as a virus that can be engineered with oncotropic properties (see Yu et al. (1999) Cancer Res. 59:1498–1504; Alemany et al. (2000) Nat. Biotechnol. 18:723–727; and Hallenbeck et al. (1999) Hum. Gene Ther. 10:1721–1733). An area that is of interest is the development of replication competent adenovirus vectors designed to selectively replicate in tumor cells. Improving the delivery of these adenoviruses, both to local-regional and disseminated disease, as well as improving the virus to promote intratumoral spread are of particular interest.

Several experimental cancer therapies utilize various aspects of adenovirus or adenovirus vectors. See, for example, U.S. Pat. No. 5,846,945; U.S. Pat No. 5,801,029; PCT/US99/08592; U.S. Pat. No. 5,747,469; PCT/US98/03514; and PCT/US97/22036.

Although replication competent adenoviruses may be able to achieve selective targeting and amplification for the treatment of local and disseminated cancer, there remains a need for improvement in both the adenovirus vectors themselves and methods for their use. Preliminary results suggest that the features of effective treatment strategies for various types of cancer will require development of specific adenovirus vectors and/or methods particular to the type of cancer under treatment. Although chemotherapy and immunotherapy are the most prevalent current therapeutic strategies for disseminated tumors, both toxic side effects and lack of efficacy remain a problem.

SUMMARY OF THE INVENTION

The present invention provides replication-competent adenoviral vectors comprising a melanoma cell-specific transcriptional regulatory element (TRE) operably linked to a gene required for virus replication. The melanoma cell-specific TRE may comprise one or more regulatory sequences, e.g. enhancers, promoters, and the like, which may be derived from the same or different genes. The adenovirus vectors may comprise co-transcribed first and second adenoviral genes under control of a melanoma cell-specific TRE, wherein the second gene is under translational control of an internal ribosome entry site (IRES). Methods are provided for introducing into a cell an adenoviral vector comprising a melanoma cell-specific TRE operably linked to a gene required for virus replication, and host cells comprising the adenovirus vector(s). In another aspect, methods are provided for conferring selective cytotoxicity in target melanoma cells, comprising contacting the cells with an adenovirus vector of the invention, whereby the vector enters the cell and propagates virus.

DETAILED DESCRIPTION OF THE EMBODIMENTS

Figure 1:
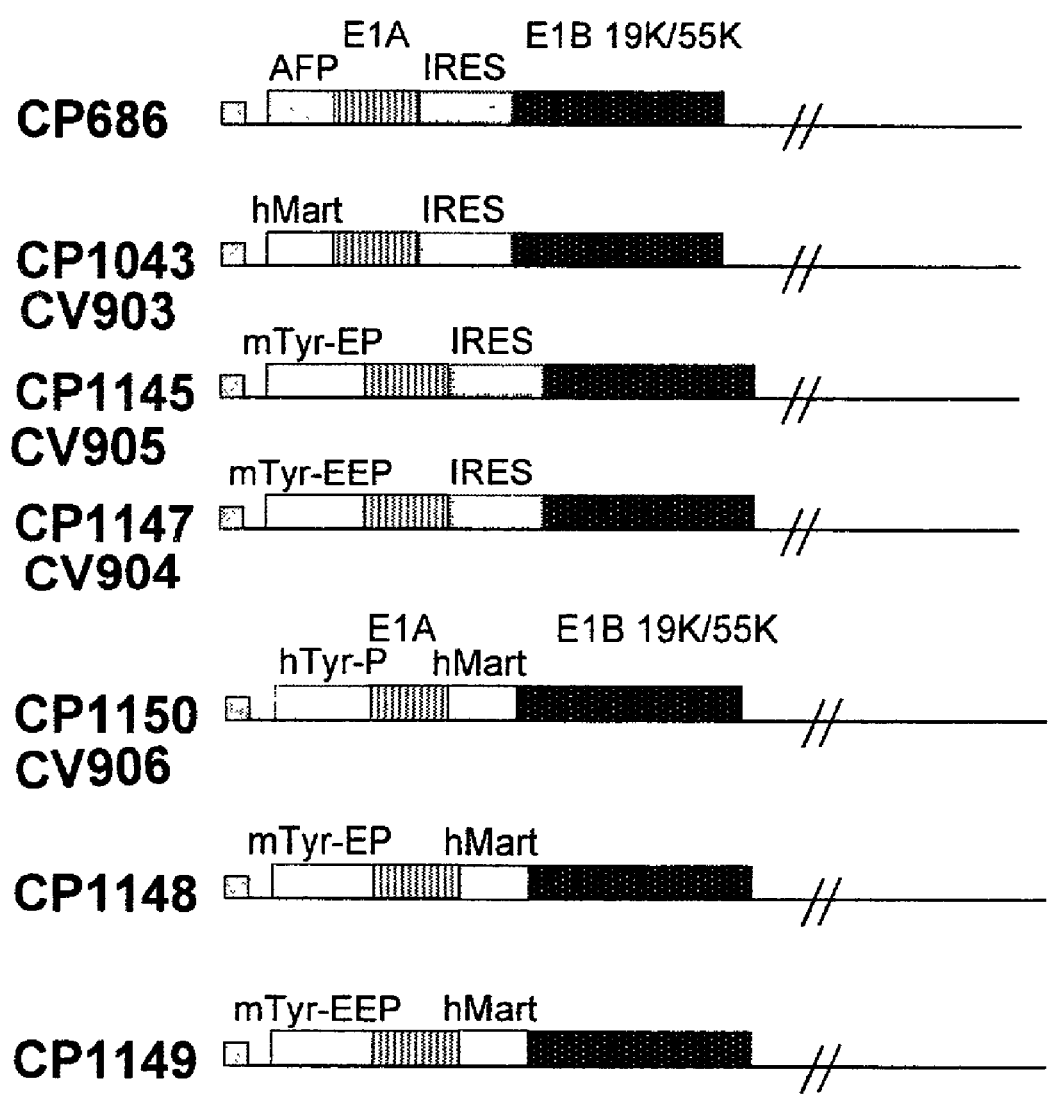
FIG. 1. is a schematic depicting structures of control and melanoma-specific adenoviruses: CV903 (CP1043), which comprises the human MART promoter (hMART); CV905 (CP1145), which comprises the murine tyrosinase gene enhancer and promoter (mEP); CV904 (CP1147), which comprises two murine tyrosinase gene enhancers and one promoter (mEEP); CV906 (CP1150), which comprises the human tyrosinase promoter (hTYR) and the human MART promoter (hMART); CP686, which comprises the alpha fetoprotein enhancer and promoter (AFP); CP1148 which comprises murine tyrosinase gene enhancer and promoter (mTyr-EP) to control E1A and the human MART promoter (hMART) to control E1B; and CP1149 which comprises tandem murine tyrosinase gene enhancers and promoter (mTyr-EEP) to control E1A and the human MART promoter (hMART) to control E1B.

The melanoma cell-specific replication-competent adenovirus vectors of the invention comprise an adenovirus gene essential for replication, preferably an early gene, under the transcriptional control of a melanoma cell-specific transcriptional regulatory element (TRE). By providing one or more melanoma cell type-specific TREs, the adenovirus vectors effect selective replication and corresponding cytotoxicity in melanoma cells. The melanoma cell-specific TRE may comprise one or more regulatory sequences, e.g. enhancers, promoters, and the like, which may be derived from the same or different genes. The adenovirus vectors may comprise co-transcribed first and second genes under control of a melanoma cell-specific TRE, wherein the second gene is under translational control of an internal ribosome entry site (IRES). In some cases, the adenovirus vectors comprise more than two co-transcribed genes under control of a melanoma cell-specific TRE, wherein one or more genes is under translational control of an internal ribosome entry site (IRES). The adenovirus vectors of the invention may or may not comprise the adenoviral E3 gene, an E3 sequence, or a portion thereof.

In another aspect, methods are provided for conferring selective cytotoxicity in target melanoma cells, comprising contacting the cells with an adenovirus vector of the invention, whereby the vector enters the cell and propagates virus. The replication of virus in melanoma cells, as compared to non-melanoma tumor cells, or to normal, i.e. non-transformed, skin cells, is typically about 10 fold greater, and may be about 100 fold greater, and in some instances is as much as about 1000 fold or more greater. The administration of virus may be combined with additional treatment (s) appropriate to the particular disease, e.g. chemotherapy, radiation therapy or immunotherapy. In some embodiments, this treatment suppresses tumor growth, e.g. by killing tumor cells. In other embodiments, the size and/or extent of a tumor is reduced, or its development delayed. Cytotoxicity is a term well understood in the art and refers to a state in which a cell's usual biochemical or biological activities are compromised (i.e., inhibited), including cell death and/or cytolysis. These activities include, but are not limited to, metabolism; cellular replication; DNA replication; transcription; translation; uptake of molecules. Assays known in the art as indicators of cytotoxicity, include dye exclusion, $^3$H-thymidine uptake, and plaque assays.

Individuals suitable for treatment by these methods include individuals who have or are suspected of having melanoma, including individuals in the early or late stages of the disease, as well as individuals who have previously been treated (e.g., are in the adjuvant setting). Other individuals suitable for the methods described herein are those who are considered high risk for developing melanoma, such as those who have a genetic predisposition and/or who have been exposed to an agent(s) which is correlated with development of melanoma. Treatment regimes include both the eradication of tumors or other forms of the disease as well as palliation of the disease. The presence of melanoma and the suitability of the individual for receiving the methods described herein may be determined by any of the techniques known in the art, including diagnostic methods such as imaging techniques, analysis of serum tumor markers, and biopsy.

The various methods of the invention will be described below. Certain embodiments of the methods use the melanoma cell-specific adenoviral vectors CV859; CV855; CV903; CV904; CV904; CV906, as described herein. A summary of the components of these vectors is included in the Examples section. Although particular methods of tumor suppression are exemplified in the discussion below, it is understood that any of a number of alternative methods, including those described above are equally applicable and suitable for use in practicing the invention. It will also be understood that an evaluation of the vectors and methods of the invention may be carried out using procedures standard in the art, including the diagnostic and assessment methods described above.

The practice of the present invention will employ, unless otherwise indicated, conventional techniques of molecular biology (including recombinant techniques), microbiology, cell biology, biochemistry and immunology, which are within the scope of those of skill in the art. Such techniques are explained fully in the literature, such as, "Molecular Cloning: A Laboratory Manual", second edition (Sambrook et al., 1989); "Oligonucleotide Synthesis" (M. J. Gait, ed., 1984); "Animal Cell Culture" (R. I. Freshney, ed., 1987); "Methods in Enzymology" (Academic Press, Inc.); "Handbook of Experimental Immunology" (D. M. Weir & C. C. Blackwell, eds.); "Gene Transfer Vectors for Mammalian Cells" (J. M. Miller & M. P. Calos, eds., 1987); "Current Protocols in Molecular Biology" (F. M. Ausubel et al., eds., 1987); "PCR: The Polymerase Chain Reaction", (Mullis et al., eds., 1994); and "Current Protocols in Immunology" (J. E. Coligan et al., eds., 1991).

For techniques related to adenovirus, see, inter alia, Feigner and Ringold (1989) Nature 337:387–388; Berkner and Sharp (1983) Nucl. Acids Res. 11:6003–6020; Graham (1984) EMBO J. 3:2917–2922; Bett et al. (1993) J. Virology 67:5911–5921; Bett et al. (1994) Proc. Natl. Acad. Sci. USA 91:8802–8806.

DEFINITIONS

Unless otherwise indicated, all terms used herein have the same meaning as they would to one skilled in the art and the practice of the present invention will employ, conventional techniques of microbiology and recombinant DNA technology, which are within the knowledge of those of skill of the art.

As used herein, the terms "neoplastic cells", "neoplasia", "tumor", "tumor cells", "cancer" and "cancer cells", (used interchangeably) refer to cells which exhibit relatively autonomous growth, so that they exhibit an aberrant growth phenotype characterized by a significant loss of control of cell proliferation. Neoplastic cells can be malignant or benign.

"Melanoma" is a malignant tumor of melanocytes, cells that are derived from the neural crest. The microstage of malignant melanoma is determined by the vertical thickness in millimeters (Breslow's classification) and/or the anatomic level of local invasion (Clark's classification) on histologic examination. In addition to treatment with the methods of the invention, melanoma metastatic to distant lymph node-bearing areas may be palliated by various treatments as known in the art. Surgical methods may include regional lymphadenectomy; isolated metastases to the lung, GI tract, bone, or occasionally the brain may be palliated by resection. Radiation therapy may provide symptomatic relief for metastases to brain, bones, and viscera. Chemotherapy presently used for treatment of melanoma, which may be combined with the present methods, includes administration of dacarbazine (DTIC) and the nitrosoureas, carmustine (BCNU) and lomustine (CCNU). Other agents include vinca alkaloids, platinum compounds, and taxanes. Biologic therapies previously shown to have activity against melanoma include interferon alpha (IFN-A) and interleukin-2 (IL-2).

Cutaneous melanoma is a distinct clinical and histologic entity. Clinical features of de novo pigmented lesions suggestive of melanoma include asymmetry, border irregularity, color variegation, and diameter greater than 6 millimeters. Melanoma has classically been divided into subtypes: superficial spreading melanoma (SSM) is the most common subtype, located on any anatomic site, and with the above typical clinical features described for melanoma. Nodular melanoma (NM) presents as an elevated or polyploid lesion on any anatomic site. It may be uniform in pigmentation and frequently shows ulceration when advanced. Lentigo maligna melanoma (LMM) occurs as a macular lesion on sun-exposed skin (head, neck), often in elderly patients. Acral lentiginous melanoma (ALM) presents as a darkly pigmented, flat to nodular lesion on palms, soles, and subungually.

Fully developed melanoma has cohesive clusters and single a typical melanocytes at the dermal-epidermal junction. Single melanocytes and clusters of melanocytes are dispersed through the full thickness of the epidermis. The invasive component forms an asymmetric lesion in the dermis, composed of a typical epithelioid and/or spindled melanocytes with an increased nuclear/cytoplasmic ratio; pleiomorphic nuclei showing prominent nucleoli and mitoses, sometimes a typical; and abundant eosinophilic cytoplasm. There is no evidence of maturation from the superficial to deep component of the lesion. An associated inflammatory response, including tumor-infiltrating lymphocytes, is often present. Occasionally, angiolymphatic invasion and/or satellite nodules can be identified. Features of regression, including the presence of melanophages, lymphocytes, fibrosis, and vascular ectasia, with absence or degeneration of melanocytes in the papillary dermis, sometimes with no overlying intraepidermal component, may be present.

Familial patterns of melanoma exist, where there can be a genetic predisposition to the disease. Persons with a typical moles and a positive family history of melanoma (at least one other affected family member) are at unusually high risk of developing melanoma. Patients with xeroderma pigmentosum, a rare genetic disorder, have a high incidence of melanoma. Some families are affected with an inherited familial a typical mole and melanoma (FAM-M) syndrome, where persons with this syndrome may have a lifetime risk as high as 100 percent of developing the disease.

As used herein, "suppressing tumor growth" refers to reducing the rate of growth of a tumor, halting tumor growth completely, causing a regression in the size of an existing tumor, eradicating an existing tumor and/or preventing the occurrence of additional tumors upon treatment with the compositions, kits or methods of the present invention. "Suppressing" tumor growth indicates a growth state that is curtailed when compared to growth without contact with, i.e., transfection by, an adenoviral vector combined with administration of chemotherapeutic agents and radiation as described herein. Tumor cell growth can be assessed by any means known in the art, including, but not limited to, measuring tumor size, determining whether tumor cells are proliferating using a $^3$H-thymidine incorporation assay, or counting tumor cells. "Suppressing" tumor cell growth means any or all of the following states: slowing, delaying, and stopping tumor growth, as well as tumor shrinkage.

"Delaying development" of a tumor means to defer, hinder, slow, retard, stabilize, and/or postpone development of the disease. This delay can be of varying lengths of time, depending on the history of the disease and/or individual being treated.

As used herein, a "transcription response element" or "transcriptional regulatory element", or "TRE" is a polynucleotide sequence, preferably a DNA sequence, comprising one or more enhancer(s) and/or promoter(s), which increases transcription of an operably linked polynucleotide sequence in a host cell that allows that TRE to function. A "melanoma cell-specific transcriptional response element" is preferentially functional in melanoma cells. It follows that a melanoma cell-specific TRE will not be preferentially active in such cells as epidermal cells, keratinocytes, epithelial cells, and the like. "Under transcriptional control" is a term well understood in the art and indicates that transcription of a polynucleotide sequence, usually a DNA sequence, depends on its being operably (operatively) linked to an element which contributes to the initiation of, or promotes, transcription. "Operably linked" refers to a juxtaposition wherein the elements are in an arrangement allowing them to function.

By "transcriptional activation" or an "increase in transcription," it is intended that transcription is increased above basal levels in the melanoma cell by at least about 2 fold, preferably at least about 5 fold, preferably at least about 10 fold, more preferably at least about 20 fold, more preferably at least about 50 fold, more preferably at least about 100 fold, more preferably at least about 200 fold, even more preferably at least about 400 fold to about 500 fold, even more preferably at least about 1000 fold. Basal levels are generally the level of activity (if any) in a non-target cell (i.e., a different cell type), or the level of activity (if any) of a reporter construct lacking a melanoma cell-specific TRE as tested in a target cell line. When the TRE controls a gene necessary for viral replication, the replication of virus is significantly higher in the target melanoma cells, as compared to a control cell, usually at least about 2-fold higher, preferably, at least about 5-fold higher, more preferably, at least about 10-fold higher, still more preferably at least about 50-fold higher, even more preferably at least about 100-fold higher, still more preferably at least about 400- to 500-fold higher, still more preferably at least about 1000-fold higher, most preferably at least about $1\times10^6$ higher. Most preferably, the adenovirus replicates solely in the target cells (that is, does not replicate or replicates at a very low levels in non-target cells).

Activity of a TRE can be determined, for example, as follows. A TRE polynucleotide sequence or set of such sequences can be generated using methods known in the art, such as chemical synthesis, site-directed mutagenesis, PCR, and/or recombinant methods. The sequence(s) to be tested can be inserted into a vector containing a promoter (if no promoter element is present in the TRE) and an appropriate reporter gene encoding a reporter protein, including, but not limited to, chloramphenicol acetyl transferase (CAT), β-galactosidase (encoded by the lacZ gene), luciferase (encoded by the luc gene), alkaline phosphatase (AP), green fluorescent protein (GFP), and horseradish peroxidase (HRP). Such vectors and assays are readily available, from, inter alia, commercial sources. Plasmids thus constructed are transfected into a suitable host cell to test for expression of the reporter gene as controlled by the putative TRE using transfection methods known in the art, such as calcium phosphate precipitation, electroporation, liposomes, DEAE dextran-mediated transfer, particle bombardment or direct injection. TRE activity is measured by detection and/or quantitation of reporter gene-derived mRNA and/or protein. Reporter protein product can be detected directly (e.g., immunochemically) or through its enzymatic activity, if any, using an appropriate substrate. Generally, to determine cell specific activity of a TRE, a TRE-reporter gene construct is introduced into a variety of cell types. The amount of TRE activity is determined in each cell type and compared to that of a reporter gene construct lacking the TRE. A TRE is determined to be cell-specific if it is preferentially functional in one cell type, compared to a different type of cell.

A melanoma specific TRE comprises a mammalian melanoma cell-specific enhancer and/or promoter. Preferred melanoma cell-specific enhancers and/or promoters for use in practicing the invention are of human, rat or mouse origin. Rodent and human 5' flanking sequences from genes expressed specifically or preferentially in melanoma cells have been described in the literature and are thus made available for practice of this invention and need not be described in detail herein. Transcriptional regulatory sequences of interest known to confer specificity include the promoter and enhancer elements from tyrosinase as discussed below; tyrosinase-related protein 2 (TRP2) (see, for example, Amae et al. (2000) *Biochim Biophys Acta* 1492 (2–3):505–8, and Yokoyama et al. (1994) *J. Biol. Chem.* 269:27080–27087); MIA protein (see Golob et al. (2000) *J Invest Dermatol* 115(1):42–7); a basic-helix-loop-helix/leucine zipper-containing transcription factor, MITF (microphthalmia associated transcription factor) was reported to be involved in transcriptional activation of tyrosinase and TRP-1 genes (Carreira et al. (2000) *J Biol Chem* 275(29): 21920–7, Yasumoto et al. (1997) *J. Biol. Chem.* 272:503–509); melanocyte-specific gene 1 (see Fenner et al. (1998) *Genomics* 51(3):401–7); melanocyte-specific tyrosinase-related protein-1 (see Galibert et al. (1999) *J Biol Chem* 274(38):26894–900); etc. A human MART-1 promoter region has been described and deposited as GenBank Accession No. U55231. Melanocyte-specific promoter activity was found in a 233-bp fragment of the human MART-1 gene 5' flanking region (Butterfield et al. (1997) *Gene* 191: 129–134).

A promoter and other control elements in the human tyrosinase gene 5' flanking region have been described and sequences have been deposited as GenBank Accession Nos. X16073 and D10751 (see Kikuchi et al. (1989) *Biochim. Biophys. Acta* 1009:283–286; and Shibata et al. (1992) *J. Biol. Chem.* 267:20584–20588). A cis-acting element has been defined that enhances melanocyte-specific expression of the human tyrosinase gene. This element comprises a 20-bp-sequence known as tyrosinase distal element (TDE), contains a CATGTG motif, and lies at positions about −1874 to about −1835 relative to the human tyrosinase gene transcription start site (Yasumoto et al. (1994) *Mol. Cell. Biol.* 14:8058–8070). A promoter region comprising sequences from about −209 to +61 of the human tyrosinase gene was found to direct melanocyte-specific expression (Shibata (1992)). Similarly, the mouse tyrosinase 5' flanking region has been analyzed and a sequence deposited as GenBank Accession Nos. D00439 and X51743 (Klüppel et al. (1991) *Proc. Natl. Acad. Sci. USA* 88:3777–3788). A minimal promoter has been identified for the mouse TRP-1 gene, and was reported to encompass nucleotides −44 to +107 relative to the transcription start site (Lowings et al. (1992) *Mol. Cell. Biol.* 12:3653–3662).

In some embodiments, a melanocyte-specific TRE comprises sequences derived from the 5' flanking region of a human tyrosinase gene, as exemplified by the TRE presented as SEQ ID NO:16. In some of these embodiments, the melanocyte-specific TRE comprises tyrosinase nucleotides from about −231 to about +65 relative to the transcription start site and may further comprise nucleotides from about −1956 to about −1716 relative to the human tyrosinase transcription start site. A tyrosinase TRE can comprise nucleotides from about −231 to about +65 juxtaposed to nucleotides from about −1956 to about −1716. It has been reported that nucleotides from about −1956 to about −1716 relative to the human tyrosinase transcription start site can confer melanocyte-specific expression of an operably linked reporter gene with either a homologous or a heterologous promoter. Accordingly, in some embodiments, a melanocyte-specific TRE comprises nucleotides from about −1956 to about −1716 operably linked to a heterologous promoter.

A melanoma-specific TRE can also comprise multimers. For example, a melanocyte-specific TRE can comprise a tandem series of at least two, at least three, at least four, or at least five promoter fragments. Alternatively, a melanocyte-specific TRE could have one or more promoter regions along with one or more enhancer regions. These multimers may also contain heterologous promoter and/or enhancer sequences.

The promoter and enhancer components of a melanoma cell-specific TRE may be in any orientation and/or distance from the coding sequence of interest, as long as the desired target cell-specific transcriptional activity is obtained. Transcriptional activation can be measured in a number of ways known in the art, but is generally measured by detection and/or quantitation of mRNA or the protein product of the coding sequence under control of (i.e., operably linked to) the melanoma cell-specific TRE. As discussed herein, a melanoma cell-specific TRE can be of varying lengths, and of varying sequence composition.

The term "composite TRE" refers to a TRE that comprises transcriptional regulatory elements that are not naturally found together, usually providing a non-native combination of promoters and enhancer, for example, a heterologous combination of promoter and enhancer, such as a combination of promoter from a tyrosinase gene and enhancer from MART; a MART enhancer and tyrosinase promoter; a combination of human and mouse promoter and enhancer; two or more enhancers in combination with a promoter; multimers of the foregoing; and the like. At least one of the promoter or enhancer elements will be melanoma cell specific, for example a tyrosinase or MART enhancer in combination with a strong promoter such as CMV or SV-40 late promoter, or a cell-status specific promoter or enhancer. In other embodiments, two or more of the elements will provide melanoma cell specificity.

As used herein, the term "cell status-specific TRE" is preferentially functional, i.e. confers transcriptional activation on an operably linked polynucleotide in a cell that exhibits a particular physiological condition, including, but not limited to, an aberrant physiological state. "Cell status" thus refers to a given, or particular, physiological state (or condition) of a cell, which is reversible and/or progressive. The physiological state may be generated internally or externally; for example, it may be a metabolic state (such as in response to conditions of low oxygen), or it may be generated due to heat or ionizing radiation. "Cell status" is distinct from a "cell type", which relates to a differentiation state of a cell, which under normal conditions is irreversible. A number of genes have been described which are expressed in association with cell status, examples of which include, but are not limited to: a cell cycle-associated gene such as E2F-1 (wherein a cell cycle-activated TRE is an E2F1 TRE); a gene associated with hypoxic conditions, e.g., hypoxia inducible factor-1 (HIF-1), which interacts with a hypoxia-responsive element (HRE) in a regulatory region of several genes; a heat-inducible gene; and a gene responsive to radiation exposure, including ionizing radiation and UV radiation, such as the early growth response-1 (Egr-1) gene which contains an element inducible by ionizing radiation. (See, e.g., Hallahan et al. (1995) *Nat Med.* 1:786–791; and Tsai-Morris et al. (1988) *Nucl. Acids. Res.* 16:8835–8846.) Generally (but not necessarily), as discussed herein, a cell status is embodied in an aberrant physiological state, examples of which are given below.

As is known in the art, activity of TREs can be inducible. Inducible TREs generally exhibit low activity in the absence of inducer, and are up-regulated in the presence of inducer. Inducers include, for example, nucleic acids, polypeptides, small molecules, organic compounds and/or environmental conditions such as temperature, pressure or hypoxia. Inducible TREs may be preferred when expression is desired only at certain times or at certain locations, or when it is desirable to titrate the level of expression using an inducing agent.

A TRE for use in the present vectors may or may not comprise a silencer. The presence of a silencer (i.e., a negative regulatory element known in the art) can assist in shutting off transcription (and thus replication) in non-target cells. Thus, the presence of a silencer can confer enhanced cell-specific vector replication by more effectively preventing replication in non-target cells. Alternatively, the lack of a silencer may stimulate replication in target cells, thus conferring enhanced target cell-specificity.

A "functionally-preserved variant" of a melanoma cell-specific TRE differs, usually in sequence, but still retains the biological activity, e.g., target cell-specific transcription activity of the corresponding native or parent melanoma cell-specific TRE, although the degree of activation may be altered. The difference in sequence may arise from, for example, single base mutation(s), addition(s), deletion(s), and/or modification(s) of the bases. The difference can also arise from changes in the sugar(s), and/or linkage(s) between the bases of a melanoma cell-specific TRE. For example, certain point mutations within sequences of TREs have been shown to decrease transcription factor binding and stimulation of transcription (see Blackwood, et al. (1998) *Science* 281:60–63, and Smith et al. (1997) *J. Biol. Chem.* 272: 27493–27496). One of skill in the art would recognize that some alterations of bases in and around transcription factor binding sites are more likely to negatively affect stimulation of transcription and cell-specificity, while alterations in bases that are not involved in transcription factor binding are not as likely to have such effects. Certain mutations are also capable of increasing TRE activity. Testing of the effects of altering bases may be performed in vitro or in vivo by any method known in the art, such as mobility shift assays, or transfecting vectors containing these alterations in TRE functional and TRE non-functional cells. Additionally, one of skill in the art would recognize that point mutations and deletions can be made to a TRE sequence without altering the ability of the sequence to regulate transcription. It will be appreciated that typically a "functionally-preserved variant" of a melanoma cell-specific TRE will hybridize to the parent sequence under conditions of high stringency. Exemplary high stringency conditions include hybridization at about 65° C. in about 5×SSPE and washing at about 65° C. in about 0.1×SSPE (where 1×SSPE=0.15 sodium chloride, 0.010 M sodium phosphate, and 0.001 M disodium EDTA). Further examples of high stringency conditions are provided in: Maniatis, et al., *MOLECULAR CLONING: A LABORATORY MANUAL,* 2d Edition (1989); and Ausubel, F. M., et al., Eds., *CURRENT PROTOCOLS IN MOLECULAR BIOLOGY,* John Wiley & Sons, Inc., Copyright (c)1987, 1988, 1989, 1990 by Current Protocols, both of which are hereby incorporated by reference.

In some instances, a "functionally-preserved variant" of a melanoma cell-specific TRE is a fragment of a native or parent melanoma cell-specific TRE. The term "fragment," when referring to melanoma cell-specific TRE, refers to a sequence that is the same as part of, but not all of, the nucleic acid sequence of a native or parental melanoma cell-specific TRE. Such as fragment either exhibits essentially the same biological function or activity as the native or parental melanoma cell-specific TRE; for example, a fragment which retains the target cell-specific transcription activity of the corresponding native or parent melanoma cell-specific TRE, although the degree of activation may be altered.

As used herein, an "internal ribosome entry site" or "IRES" refers to an element that promotes direct internal ribosome entry to the initiation codon, such as ATG, of a cistron (a protein encoding region), thereby leading to the cap-independent translation of the gene (Jackson et al. (1990) *Trends Biochem Sci* 15(12):477–83) and Jackson et al. (1995) *RNA* 1(10):985–1000). The present invention encompasses the use of any IRES element that is able to direct internal ribosome entry to the initiation codon of a cistron. "Under translational control of an IRES" as used herein means that translation is associated with the IRES and proceeds in a cap-independent manner. Examples of "IRES" known in the art include, but are not limited to IRES obtainable from picornavirus (Jackson et al., 1990, *Trends Biochem Sci* 15(12):477–483); and IRES obtainable from viral or cellular mRNA sources, such as for example, immunogloublin heavy-chain binding protein (BiP), the vascular endothelial growth factor (VEGF) (Huez et al. (1998) *Mol. Cell. Biol.* 18(11):6178–6190), the fibroblast growth factor 2, and insulin-like growth factor, the translational initiation factor eIF4G, yeast transcription factors TFIID and HAP4. IRES have also been reported in different viruses such as cardiovirus, rhinovirus, aphthovirus, HCV, Friend murine leukemia virus (FrMLV) and Moloney murine leukemia virus (MoMLV). As used herein, the term "IRES" encompasses functional variations of IRES sequences as long as the variation is able to promote direct internal ribosome entry to the initiation codon of a cistron. In preferred embodiments, the IRES is mammalian. In other embodiments, the IRES is viral or protozoan. In one illustrative embodiment disclosed herein, the IRES is obtainable from encephelomycarditis virus (ECMV) (commercially available from Novogen, Duke et al. (1992) J. Virol 66(3): 1602–1609). In another illustrative embodiment disclosed herein, the IRES is from VEGF. In some embodiments, an adenovirus vector comprising an IRES and a target cell-specific TRE exhibits greater specificity for the target cell than an adenovirus vector comprising a target cell-specific TRE and lacking an IRES.

In some embodiments, specificity is conferred by preferential transcription and/or translation of the first and second genes due to the presence of a target cell specific TRE. In other embodiments, specificity is conferred by preferential replication of the adenovirus vectors in target cells due to the target cell-specific TRE driving transcription of a gene essential for replication.

An "E3 region" (used interchangeably with "E3") is a term well understood in the art and means the region of the adenoviral genome that encodes the E3 gene products. Generally, the E3 region is located between about nucleotides 28583 and 30470 of the adenoviral genome. The E3 region has been described in various publications, including, for example, Wold et al. (1995) Curr. Topics Microbiol. Immunol. 199:237–274. A "portion" of the E3 region means less than the entire E3 region, and as such includes polynucleotide deletions as well as polynucleotides encoding one or more polypeptide products of the E3 region.

A "multicistronic transcript" refers to an mRNA molecule that contains more than one protein coding region, or cistron. A mRNA comprising two coding regions is denoted a "bicistronic transcript." The "5'-proximal" coding region or cistron is the coding region whose translation initiation codon (usually AUG) is closest to the 5'-end of a multicistronic mRNA molecule. A "5'-distal" coding region or cistron is one whose translation initiation codon (usually AUG) is not the closest initiation codon to the 5' end of the mRNA. The terms "5'-distal" and "downstream" are used synonymously to refer to coding regions that are not adjacent to the 5' end of a mRNA molecule.

As used herein, "co-transcribed" means that two (or more) coding regions of polynucleotides are under transcriptional control of a single transcriptional control element.

As used herein, the term "vector" refers to a polynucleotide construct designed for transduction/transfection of one or more cell types. Vectors may be, for example, "cloning vectors" which are designed for isolation, propagation and replication of inserted nucleotides, "expression vectors" which are designed for expression of a nucleotide sequence in a host cell, or a "viral vector" which is designed to result in the production of a recombinant virus or virus-like particle, or "shuttle vectors", which comprise the attributes of more than one type of vector. "Under transcriptional control" is a term well understood in the art and indicates that transcription of a polynucleotide sequence, usually a DNA sequence, depends on its being operably (operatively) linked to an element which contributes to the initiation of, or promotes, transcription. "Operably linked" refers to a juxtaposition wherein the elements are in an arrangement allowing them to function.

An "adenovirus vector" or "adenoviral vector" (used interchangeably) of the invention is a polynucleotide construct, which is replication competent, exhibits preferential replication in melanoma cells and contains a tissue-specific transcriptional regulatory sequence linked to an adenoviral gene. In some embodiments, an adenoviral vector of the invention includes a therapeutic gene sequence, e.g., a cytokine gene sequence. Exemplary adenoviral vectors of the invention include, but are not limited to, DNA, DNA encapsulated in an adenovirus coat, adenoviral DNA packaged in another viral or viral-like form (such as herpes simplex, and AAV), adenoviral DNA encapsulated in liposomes, adenoviral DNA complexed with polylysine, adenoviral DNA complexed with synthetic polycationic molecules, conjugated with transferrin, or complexed with compounds such as PEG to immunologically "mask" the antigenicity and/or increase half-life, or conjugated to a nonviral protein.

The terms "polynucleotide" and "nucleic acid", used interchangeably herein, refer to a polymeric form of nucleotides of any length, either ribonucleotides or deoxyribonucleotides. These terms include a single-, double- or triple-stranded DNA, genomic DNA, cDNA, RNA, DNA-RNA hybrid, or a polymer comprising purine and pyrimidine bases, or other natural, chemically, biochemically modified, non-natural or derivatized nucleotide bases. Preferably, an adenoviral polynucleotide is DNA. As used herein, "DNA" includes not only bases A, T, C, and G, but also includes any of their analogs or modified forms of these bases, such as methylated nucleotides, internucleotide modifications such as uncharged linkages and thioates, use of sugar analogs, and modified and/or alternative backbone structures, such as polyamides. For purposes of this invention, adenovirus vectors are replication-competent in a melanoma target cell.

The following are non-limiting examples of polynucleotides: a gene or gene fragment, exons, introns, mRNA, tRNA, rRNA, ribozymes, cDNA, recombinant polynucleotides, branched polynucleotides, plasmids, vectors, isolated DNA of any sequence, isolated RNA of any sequence, nucleic acid probes, and primers. A polynucleotide may comprise modified nucleotides, such as methylated nucleotides and nucleotide analogs, uracyl, other sugars and linking groups such as fluororibose and thioate, and nucleotide branches. The sequence of nucleotides may be interrupted by non-nucleotide components. A polynucleotide may be further modified after polymerization, such as by conjugation with a labeling component. Other types of modifications included in this definition are caps, substitution of one or more of the naturally occurring nucleotides with an analog, and introduction of means for attaching the polynucleotide to proteins, metal ions, labeling components, other polynucleotides, or a solid support. Preferably, the polynucleotide is DNA. As used herein, "DNA" includes not only bases A, T, C, and G, but also includes any of their analogs or modified forms of these bases, such as methylated nucleotides, internucleotide modifications such as uncharged linkages and thioates, use of sugar analogs, and modified and/or alternative backbone structures, such as polyamides.

A polynucleotide or polynucleotide region has a certain percentage (for example, 80%, 85%, 90%, or 95%) of "sequence identity" to another sequence means that, when aligned, that percentage of bases are the same in comparing the two sequences. This alignment and the percent homology or sequence identity can be determined using software programs known in the art, for example those described in *Current Protocols in Molecular Biology* (F. M. Ausubel et al., eds., 1987) Supplement 30, section 7.7.18. A preferred alignment program is ALIGN Plus (Scientific and Educational Software, Pennsylvania), preferably using default parameters, which are as follows: mismatch=2; open gap=0; extend gap=2.

In the context of adenovirus, a "heterologous polynucleotide" or "heterologous gene" or "transgene" is any polynucleotide or gene that is not present in wild-type adenovirus. Preferably, the transgene will also not be expressed or present in the target cell prior to introduction by the adenovirus vector. Examples of preferred transgenes for inclusion in the adenovirus vectors of the invention, are provided below.

In the context of adenovirus, a "heterologous" promoter or enhancer is one which is not associated with or derived from an adenovirus gene.

In the context of a target cell-specific TRE, a "heterologous" promoter or enhancer is one which is derived from a gene other than the gene from which a particular target cell-specific TRE is derived.

In the context of adenovirus, an "endogenous" promoter, enhancer, or TRE is native to or derived from adenovirus.

"Replication" and "propagation" are used interchangeably and refer to the ability of an adenovirus vector of the invention to reproduce or proliferate. These terms are well understood in the art. For purposes of this invention, replication involves production of adenovirus proteins and is generally directed to reproduction of adenovirus. Replication can be measured using assays standard in the art and described herein, such as a virus yield assay, burst assay or plaque assay. "Replication" and "propagation" include any activity directly or indirectly involved in the process of virus manufacture, including, but not limited to, viral gene expression; production of viral proteins, nucleic acids or other components; packaging of viral components into complete viruses; and cell lysis.

"Preferential replication" and "selective replication" may be used interchangeably and mean that an adenovirus replicates more in a target cell than in a non-target cell. Preferably, the adenovirus replicates at a significantly higher rate in target cells than non target cells; preferably, at least about 5-fold higher, more preferably, at least about 10-fold higher, still more preferably at least about 50fold higher, even more preferably at least about 100-fold higher, still more preferably at least about 400- to 500-fold higher, still more preferably at least about 1000-fold higher, most preferably at least about $1 \times 10^6$ higher. Most preferably, the adenovirus replicates only in the target cells (that is, does not replicate at all or replicates at a very low level in non-target cells).

An "individual" is a vertebrate, preferably a mammal, more preferably a human. Mammals include, but are not limited to, farm animals, sport animals, rodents, primates, and pets. A "host cell" includes an individual cell or cell culture which can be or has been a recipient of an adenoviral vector(s) of this invention. Host cells include progeny of a single host cell, and the progeny may not necessarily be completely identical (in morphology or in total DNA complement) to the original parent cell due to natural, accidental, or deliberate mutation and/or change. A host cell includes cells transfected or infected in vivo or in vitro with an adenoviral vector of this invention.

As used herein, "cytotoxicity" is a term well understood in the art and refers to a state in which a cell's usual biochemical or biological activities are compromised (i.e., inhibited). These activities include, but are not limited to, metabolism; cellular replication; DNA replication; transcription; translation; uptake of molecules. "Cytotoxicity" includes cell death and/or cytolysis. Assays are known in the art which indicate cytotoxicity, such as dye exclusion, $^3$H-thymidine uptake, and plaque assays.

The term "selective cytotoxicity", as used herein, refers to the cytotoxicity conferred by an adenovirus vector of the invention on a cell which allows or induces a target cell-specific TRE to function (referred to herein as a "target cell") when compared to the cytotoxicity conferred by an adenoviral vector of the present invention on a cell which does not allow a target cell-specific TRE to function (a "non-target cell"). Such cytotoxicity may be measured, for example, by plaque assays, by reduction or stabilization in size of a tumor comprising target cells, or the reduction or stabilization of serum levels of a marker characteristic of the tumor cells, or a tissue-specific marker, e.g., a cancer marker.

ADENOVIRAL VECTORS

The adenoviral vectors used in the methods described herein are replication-competent melanoma cell-specific adenoviral vectors comprising an adenovirus gene, preferably a gene essential for replication under transcriptional control of a melanoma cell specific TRE. The vector may or may not include an E3 region. In other embodiments, an adenovirus vector is a replication competent, melanoma cell specific vector comprising E1B, wherein E1B has a deletion of part or all of the 19-kDa region. In some embodiments the adenoviral gene essential for replication is an early gene, preferably E1A or E1B or both. In some embodiments, the adenovirus vector comprises co-transcribed first and second genes under transcriptional control of a heterologous, melanoma cell-specific transcriptional regulatory element (TRE), wherein the second gene is under translational control of an internal ribosome entry site (IRES). The adenovirus vector may further comprise E3.

The E1B 19-kDa region refers to the genomic region of the adenovirus E1B gene encoding the E1B 19-kDa product. According to wild-type Ad5, the E1B 19-kDa region is a 261bp region located between nucleotide 1714 and nucleotide 2244. The E1B 19-kDa region has been described in, for example, Rao et al., *Proc. Natl. Acad. Sci. USA*, 89:7742–7746. The present invention encompasses deletion of part or all of the E1B 19-kDa region as well as embodiments wherein the E1B 19-kDa region is mutated, as long as the deletion or mutation lessens or eliminates the inhibition of apoptosis associated with E1B-19 kDa.

The adenovirus vectors used in this invention replicate preferentially in melanoma cells, which replication preference is indicated by comparing the level of replication (i.e., titer) in melanoma cells to the level of replication in normal or control cells, in which the TRE is not active. Comparison of the adenovirus titer of a melanoma cell to the titer of a TRE inactive cell type provides a key indication that the overall replication preference is enhanced due to the replication in target melanoma cells as well as depressed replication in non-target cells. This is especially useful in the cancer context, in which targeted cell killing is desirable. Runaway infection is prevented due to the cell-specific requirements for viral replication. Without wishing to be bound by any particular theory, production of adenovirus proteins can serve to activate and/or stimulate the immune system, either generally or specifically toward target cells producing adenoviral proteins which can be an important consideration in the cancer context, where individuals are often moderately to severely immunocompromised.

In one aspect of the present invention, the adenovirus vectors comprise an intergenic IRES element(s) which links the translation of two or more genes, thereby removing any potential for homologous recombination based on the presence of identical TREs in the vector. Adenovirus vectors comprising an IRES are stable and in some embodiments provide better specificity than vectors not containing an IRES. Another advantage of an adenovirus vector comprising an intergenic IRES is that the use of an IRES rather than a second TRE may provide additional space in the vector for an additional gene(s) such as a therapeutic gene. Accordingly, in one aspect of the invention, the viral vectors disclosed herein comprise at least one IRES within a multicistronic transcript, wherein production of the multicistronic transcript is regulated by a heterologous, target cell-specific TRE. For adenovirus vectors comprising a second gene under control of an IRES, it is preferred that the endogenous promoter of a gene under translational control of an IRES be deleted so that the endogenous promoter does not interfere with transcription of the second gene. It is preferred that the second gene be in frame with the IRES if the IRES contains an initiation codon. If an initiation codon, such as ATG, is present in the IRES, it is preferred that the initiation codon of the second gene is removed and that the IRES and the second gene are in frame. Alternatively, if the IRES does not contain an initiation codon or if the initiation codon is removed from the IRES, the initiation codon of the second gene is used. In one embodiment, the adenovirus vectors comprises the adenovirus essential genes, E1A and E1B genes, under the transcriptional control of a heterologous, melanoma cell-specific TRE, and an IRES introduced between E1A and E1B. Thus, both E1A and E1B are under common transcriptional control, and translation of E1B coding region is obtained by virtue of the presence of the IRES. In one embodiment, E1A has its endogenous promoter deleted. In another embodiment, E1A has an endogenous enhancer deleted and in yet an additional embodiment, E1A has its endogenous promoter deleted and E1A enhancer I deleted. In another embodiment, E1B has its endogenous promoter deleted. In yet further embodiments, E1B has a deletion of part or all of the 19-kDa region.

An adenovirus vector may further include an additional heterologous TRE which may or may not be operably linked to the same gene(s) as the target cell-specific TRE. For example a TRE (such as a cell type-specific or cell status-specific TRE) may be juxtaposed to a second type of target-cell-specific TRE. "Juxtaposed" means a target cell-specific TRE and a second TRE transcriptionally control the same gene. For these embodiments, the target cell-specific TRE and the second TRE may be in any of a number of configurations, including, but not limited to, (a) next to each other (i.e., abutting); (b) both 5' to the gene that is transcriptionally controlled (i.e., may have intervening sequences between them); (c) one TRE 5' and the other TRE 3' to the gene.

To provide cytotoxicity to target cells, one or more transgenes having a cytotoxic effect may be present in the vector. Additionally, or alternatively, an adenovirus gene that contributes to cytotoxicity and/or cell death, such as the adenovirus death protein (ADP) gene, can be included in the vector, optionally under the selective transcriptional control of a heterologous TRE and optionally under the translational control of an IRES.

Functionally preserved variants of TREs can be used in the vectors disclosed herein. Variant TREs retain function in the target cell but need not exhibit maximal function. In fact, maximal transcriptional activation activity of a TRE may not always be necessary to achieve a desired result, and the level of induction afforded by a fragment of a TRE may be sufficient for certain applications. For example, if used for treatment or palliation of a disease state, less-than-maximal responsiveness may be sufficient if, for example, the target cells are not especially virulent and/or the extent of disease is relatively confined.

As discussed herein, a TRE can be of varying lengths, and of varying sequence composition. The size of a heterologous TRE will be determined in part by the capacity of the viral vector, which in turn depends upon the contemplated form of the vector (see infra). Generally minimal sizes are preferred for TREs, as this provides potential room for insertion of other sequences which may be desirable, such as transgenes, and/or additional regulatory sequences. In a preferred embodiment, such an additional regulatory sequence is an IRES. However, if no additional sequences are contemplated, or if, for example, an adenoviral vector will be maintained and delivered free of any viral packaging constraints, larger TRE sequences can be used as long as the resultant adenoviral vector remains replication-competent.

To minimize non-specific replication, endogenous adenovirus TREs are preferably removed from the vector. Besides facilitating target cell-specific replication, removal of endogenous TREs also provides greater insert capacity in a vector, which may be of special concern if an adenoviral vector is to be packaged within a virus particle. Even more importantly, deletion of endogenous TREs prevents the possibility of a recombination event whereby a heterologous TRE is deleted and the endogenous TRE assumes transcriptional control of its respective adenovirus coding sequences. However, endogenous TREs can be maintained in the adenovirus vector(s), provided that sufficient cell-specific replication preference is preserved. These embodiments are constructed by inserting heterologous TREs between an endogenous TRE and a replication gene coding segment. Requisite melanoma cell-specific replication preference is determined by conducting assays that compare replication of the adenovirus vector in a cell which allows function of the heterologous TREs with replication in a cell which does not.

The adenovirus vectors of this invention can be prepared using recombinant techniques that are standard in the art. Generally, a melanoma cell-specific TRE is inserted 5' to the adenoviral gene of interest, preferably an adenoviral replication gene, more preferably one or more early replication genes (although late gene(s) can be used). A melanoma cell-specific TRE can be prepared using oligonucleotide synthesis (if the sequence is known) or recombinant methods (such as PCR and/or restriction enzymes). Convenient restriction sites, either in the natural adeno-DNA sequence or introduced by methods such as PCR or site-directed mutagenesis, provide an insertion site for a melanoma cell-specific TRE. Accordingly, convenient restriction sites for annealing (i.e., inserting) a melanoma cell-specific TRE can be engineered onto the 5' and 3' ends of a UP-TRE using standard recombinant methods, such as PCR.

Adenoviral vectors containing all replication-essential elements, with the desired elements (e.g., E1A) under control of a melanoma cell-specific TRE, are conveniently prepared by homologous recombination or in vitro ligation of two plasmids, one providing the left-hand portion of adenovirus and the other plasmid providing the right-hand region, one or more of which contains at least one adenovirus gene under control of a melanoma cell-specific TRE. If homologous recombination is used, the two plasmids should share at least about 500 bp of sequence overlap. Each plasmid, as desired, may be independently manipulated, followed by cotransfection in a competent host, providing complementing genes as appropriate, or the appropriate transcription factors for initiation of transcription from a melanoma cell-specific TRE for propagation of the adenovirus. Plasmids are generally introduced into a suitable host cell such as 293 cells using appropriate means of transduction, such as cationic liposomes. Alternatively, in vitro ligation of the right and left-hand portions of the adenovirus genome can also be used to construct recombinant adenovirus derivative containing all the replication-essential portions of adenovirus genome. Berkner et al. (1983) *Nucleic Acid Research* 11: 6003–6020; Bridge et al. (1989) *J. Virol.* 63: 631–638.

For convenience, plasmids are available that provide the necessary portions of adenovirus. Plasmid pXC.1 (McKinnon (1982) *Gene* 19:33–42) contains the wild-type left-hand end of Ad5. pBHG10 (Bett et al. (1994); Microbix Biosystems Inc., Toronto) provides the right-hand end of Ad5, with a deletion in E3. The deletion in E3 provides room in the virus to insert a 3 kb melanoma cell-specific TRE without deleting the endogenous enhancer/promoter. The gene for E3 is located on the opposite strand from E4 (r-strand). pBHG11 provides an even larger E3 deletion (an additional 0.3 kb is deleted). Bett et al. (1994). Alternatively, the use of pBHGE3 (Microbix Biosystems, Inc.) provides the right hand end of Ad5, with a full-length of E3.

For manipulation of the early genes, the transcription start site of Ad5 E1A is at 498 and the ATG start site of the E1A coding segment is at 560 in the virus genome. This region can be used for insertion of a melanoma cell-specific TRE. A restriction site may be introduced by employing polymerase chain reaction (PCR), where the primer that is employed may be limited to the Ad5 genome, or may involve a portion of the plasmid carrying the Ad5 genomic DNA. For example, where pBR322 is used, the primers may use the EcoRI site in the pBR322 backbone and the XbaI site at nt 1339 of Ad5. By carrying out the PCR in two steps, where overlapping primers at the center of the region introduce a nucleotide sequence change resulting in a unique restriction site, one can provide for insertion of melanoma cell-specific TRE at that site.

A similar strategy may also be used for insertion of a melanoma cell-specific TRE element to regulate E1B. The E1B promoter of Ad5 consists of a single high-affinity recognition site for Spl and a TATA box. This region extends from Ad5 nt 1636 to 1701. By insertion of a melanoma cell-specific TRE in this region, one can provide for cell-specific transcription of the E1B gene. By employing the left-hand region modified with the cell-specific response element regulating E1A, as the template for introducing a melanoma cell-specific TRE to regulate E1B, the resulting adenovirus vector will be dependent upon the cell-specific transcription factors for expression of both E1A and E1B. In some embodiments, part or all of the 19-kDa region of E1B is deleted.

Similarly, a melanoma cell-specific TRE can be inserted upstream of the E2 gene to make its expression cell-specific. The E2 early promoter, mapping in Ad5 from 27050-27150, consists of a major and a minor transcription initiation site, the latter accounting for about 5% of the E2 transcripts, two non-canonical TATA boxes, two E2F transcription factor binding sites and an ATF transcription factor binding site (for a detailed review of the E2 promoter architecture see Swaminathan et al., *Curr. Topics in Micro. and Immunol.* (1995) 199(part 3):177–194.

The E2 late promoter overlaps with the coding sequences of a gene encoded by the counterstrand and is therefore not amenable for genetic manipulation. However, the E2 early promoter overlaps only for a few base pairs with sequences coding for a 33 kD protein on the counterstrand. Notably, the SpeI restriction site (Ad5 position 27082) is part of the stop codon for the above mentioned 33 kD protein and conveniently separates the major E2 early transcription initiation site and TATA-binding protein site from the upstream transcription factor binding sites E2F and ATF. Therefore, insertion of a melanoma cell-specific TRE having SpeI ends into the SpeI site in the 1-strand would disrupt the endogenous E2 early promoter of Ad5 and should allow melanoma cell-restricted expression of E2 transcripts.

For E4, one must use the right hand portion of the adenovirus genome. The E4 transcription start site is predominantly at about nt 35605, the TATA box at about nt 35631 and the first AUG/CUG of ORF I is at about nt 35532. Virtanen et al. (1984) *J. Virol.* 51: 822–831. Using any of the above strategies for the other genes, a UP-TRE may be introduced upstream from the transcription start site. For the construction of full-length adenovirus with a melanoma cell-specific TRE inserted in the E4 region, the co-transfection and homologous recombination are performed in W162 cells (Weinberg et al. (1983) *Proc. Natl. Acad. Sci.* 80:5383–5386) which provide E4 proteins in trans to complement defects in synthesis of these proteins.

Adenoviral constructs containing an E3 region can be generated wherein homologous recombination between an E3-containing adenoviral plasmid, for example, BHGE3 (Microbix Biosystems Inc., Toronto) and a non-E3-containing adenoviral plasmid, is carried out.

Alternatively, an adenoviral vector comprising an E3 region can be introduced into cells, for example 293 cells, along with an adenoviral construct or an adenoviral plasmid construct, where they can undergo homologous recombination to yield adenovirus containing an E3 region. In this case, the E3-containing adenoviral vector and the adenoviral construct or plasmid construct contain complementary regions of adenovirus, for example, one contains the left-hand and the other contains the right-hand region, with sufficient sequence overlap as to allow homologous recombination.

Alternatively, an E3-containing adenoviral vector of the invention can be constructed using other conventional methods including standard recombinant methods (e.g., using restriction nucleases and/or PCR), chemical synthesis, or a combination of any of these. Further, deletions of portions of the E3 region can be created using standard techniques of molecular biology.

Insertion of an IRES into a vector is accomplished by methods and techniques that are known in the art and described herein supra, including but not limited to, restriction enzyme digestion, ligation, and PCR. A DNA copy of an IRES can be obtained by chemical synthesis, or by making a cDNA copy of, for example, a picornavirus IRES. See, for example, Duke et al. (1995) *J. Virol.* 66(3):1602–9) for a description of the EMCV IRES and Huez et al. (1998), *Mol. Cell. Biol.* 18(11):6178–90) for a description of the VEGF IRES. The internal translation initiation sequence is inserted into a vector genome at a site such that it lies upstream of a 5'-distal coding region in a multicistronic mRNA. For example, in a preferred embodiment of an adenovirus vector in which production of a bicistronic E1A-E1B mRNA is under the control of a melanoma cell-specific TRE, the E1B promoter is deleted or inactivated, and an IRES sequence is placed between E1A and E1B. In other embodiments, part or all of the 19-kDa region of E1B is deleted. IRES sequences of cardioviruses and certain aphthoviruses contain an AUG codon at the 3' end of the IRES that serves as both a ribosome entry site and as a translation initiation site. Accordingly, this type of IRES is introduced into a vector so as to replace the translation initiation codon of the protein whose translation it regulates. However, in an IRES of the entero/rhinovirus class, the AUG at the 3' end of the IRES is used for ribosome entry only, and translation is initiated at the next downstream AUG codon. Accordingly, if an entero/rhinovirus IRES is used in a vector for translational regulation of a downstream coding region, the AUG (or other translation initiation codon) of the downstream gene is retained in the vector construct.

Methods of packaging polynucleotides into adenovirus particles are known in the art and are also described in co-owned PCT PCT/US98/04080.

THERAPEUTIC METHODS

An effective amount of the adenovirus vector is administered to a patient as a composition in a pharmaceutically acceptable excipient (and may or may not be in the same compositions), including, but not limited to, saline solutions, suitable buffers, preservatives, stabilizers, and may be administered in conjunction with suitable agents such as antiemetics. An effective amount is an amount sufficient to effect beneficial or desired results, including clinical results. An effective amount can be administered in one or more administrations. For purposes of this invention, an effective amount of an adenoviral vector is an amount that is sufficient to palliate, ameliorate, stabilize, reverse, slow or delay the progression of the disease state. Some individuals are refractory to these treatments, and it is understood that the methods encompass administration to these individuals. The amount to be given will be determined by the condition of the individual, the extent of disease, the route of administration, how many doses will be administered, and the desired objective.

Delivery of adenoviral vectors is generally accomplished by either site-specific injection or intravenously. Site-specific injections of vector may include, for example, injections into skin lesions, as well as intraperitoneal, intrapleural, intrathecal, intra-arterial, intra-tumor injections or topical application. These methods are easily accommodated in treatments using the combination of adenoviral vectors and chemotherapeutic agents.

The adenoviral vectors may be delivered to the target cell in a variety of ways, including, but not limited to, liposomes, general transfection methods that are well known in the art (such as calcium phosphate precipitation or electroporation), direct injection, and intravenous infusion. The means of delivery will depend in large part on the particular adenoviral vector (including its form) as well as the type and location of the target cells (i.e., whether the cells are in vitro or in vivo).

If used as a packaged adenovirus, adenovirus vectors may be administered in an appropriate physiologically acceptable carrier at a dose of about $10^4$ to about $10^{14}$. The multiplicity of infection will generally be in the range of about 0.001 to 100. If administered as a polynucleotide construct (i.e., not packaged as a virus) about 0.01 □g to about 1000 □g of an adenoviral vector can be administered. The adenoviral vector(s) may be administered one or more times, depending upon the intended use and the immune response potential of the host, and may also be administered as multiple, simultaneous injections. If an immune response is undesirable, the immune response may be diminished by employing a variety of immunosuppressants, or by employing a technique such as an immunoadsorption procedure (e.g., immunoapheresis) that removes adenovirus antibody from the blood, so as to permit repetitive administration, without a strong immune response. If packaged as another viral form, such as HSV, an amount to be administered is based on standard knowledge about that particular virus (which is readily obtainable from, for example, published literature) and can be determined empirically.

Embodiments of the present invention include methods for the administration of combinations of a melanoma cell-specific adenoviral vector and a second anti-neoplastic therapy, which may include radiation, an anti-neoplastic agent, etc., to an individual with neoplasia, as detailed in co-owned U.S. application Ser. No. 09/814,357 U.S. Pat. No. 6,911,200, expressly incorporated by reference herein. The chemotherapeutic agent and adenovirus may be administered simultaneously or sequentially, with various time intervals for sequential administration. In some embodiments, an effective amount of an adenoviral vector and an effective amount of at least one antineoplastic agent are combined with a suitable excipient and/or buffer solutions and administered simultaneously from the same solution by any of the methods listed herein or those known in the art. This may be applicable when the antineoplastic agent does not compromise the viability and/or activity of the adenoviral vector itself.

Where more than one antineoplastic agent is administered, the agents may be administered together in the same composition; sequentially in any order; or, alternatively, administered simultaneously in different compositions. If the agents are administered sequentially, administration may further comprise a time delay. Sequential administration may be in any order, and accordingly encompasses the administration of an effective amount of an adenoviral vector first, followed by the administration of an effective amount of the chemotherapeutic agent. The interval between administration of adenovirus and chemotherapeutic agent may be in terms of at least (or, alternatively, less than) minutes, hours, or days. Sequential administration also encompasses administration of a chosen antineoplastic agent followed by the administration of the adenoviral vector. The interval between administration may be in terms of at least (or, alternatively, less than) minutes, hours, or days.

Administration of the above-described methods may also include repeat doses or courses of target-cell specific adenovirus and chemotherapeutic agent depending, inter alia, upon the individual's response and the characteristics of the individual's disease. Repeat doses may be undertaken immediately following the first course of treatment (i.e., within one day), or after an interval of days, weeks or months to achieve and/or maintain suppression of tumor growth. A particular course of treatment according to the above-described methods, for example, combined adenoviral and chemotherapy, may later be followed by a course of combined radiation and adenoviral therapy.

Anti-neoplastic agents include those from each of the major classes of chemotherapeutics, including but not limited to: alkylating agents, alkaloids, antimetabolites, anti-tumor antibiotics, nitrosoureas, hormonal agonists/antagonists and analogs, immunomodulators, photosensitizers, enzymes and others. In some embodiments, the antineoplastic is an alkaloid, an antimetabolite, an antibiotic or an alkylating agent. In certain embodiments the antineoplastic agents include, for example, thiotepa, interferon alpha-2a, and the M-VAC combination (methotrexate-vinblastine, doxorubicin, cyclophosphamide). Preferred antineoplastic agents include, for example, 5-fluorouracil, cisplatin, 5-azacytidine, and gemcitabine. Particularly preferred embodiments include, but are not limited to, 5-fluorouracil, gemcitabine, doxorubicin, miroxantrone, mitomycin, dacarbazine, carmustine, vinblastine, lomustine, tamoxifen, docetaxel, paclitaxel or cisplatin. The specific choice of both the chemotherapeutic agent(s) is dependent upon, inter alia, the characteristics of the disease to be treated. These characteristics include, but are not limited to, location of the tumor, stage of the disease and the individual's response to previous treatments, if any.

In addition to the use of single antineoplastic agents in combination with a particular adenoviral vector, the invention also includes the use of more than one agent in conjunction with an adenoviral vector. These combinations of antineoplastics when used to treat neoplasia are often referred to as combination chemotherapy and are often part of a combined modality treatment which may also include surgery and/or radiation, depending on the characteristics of an individual's cancer. It is contemplated that the combined adenoviral/chemotherapy of the present invention can also be used as part of a combined modality treatment program.

There are a variety of delivery methods for the administration of antineoplastic agents, which are well known in the art, including oral and parenteral methods. There are a number of drawbacks to oral administration for a large number of antineoplastic agents, including low bioavailability, irritation of the digestive tract and the necessity of remembering to administer complicated combinations of drugs. The majority of parenteral administration of antineoplastic agents is intravenously, as intramuscular and subcutaneous injection often leads to irritation or damage to the tissue. Regional variations of parenteral injections include intra-arterial, intravesical, intra-tumor, intrathecal, intrapleural, intraperitoneal and intracavity injections.

Delivery methods for chemotherapeutic agents include intravenous, intraparenteral and introperitoneal methods as well as oral administration. Intravenous methods also include delivery through a vein of the extremities as well as including more site specific delivery, such as an intravenous drip into the portal vein of the liver. Other intraparenteral methods of delivery include direct injections of an antineoplastic solution, for example, subcutaneously, intracavity or intra-tumor.

The invention also provides combination methods which employ the adenoviral vectors as described herein and radiation. The choice of suitable radiation therapy is well known by a person skilled in the art and decided on an individual basis, and includes X-rays, gamma rays, alpha particles, beta particles, radioactive isotopes, photons, neutrons, electrons and other forms of ionizing radiation. Sources of radiation include Americium, chromic phosphate, radioactive Cobalt, $^{131}$I-ethiodized oil, Gold (radioactive, colloidal) iobenguane, Radium, Radon, sodium iodide (radioactive), sodium phosphate (radioactive), and $^{137}$Cesium. Radioimmunotherapy can also be used. In some embodiments, radiation therapy includes use of one or more radiosensitizing agent(s) or radiation protectants.

As is well known in the art, radiation therapy includes treatment with X-rays and gamma-rays, as well as alpha and beta particles, photons, electrons, neutrons, implants of radioactive isotopes and other forms of ionizing radiation. Recent experimental therapy employs monoclonal antibodies specific to the malignant tumor to deliver radioactive isotopes directly to the site of the tumor, termed radioimmunotherapy. The most common type of radiation treatment is radiation directed to the body area containing the neoplastic tumor, which is known as regional or local radiation therapy.

The combined modality treatment of radiation and target cell-specific adenoviral therapy can be carried out in a number of ways, including delivery of the adenoviral vector followed by radiation therapy, or where vector delivery is followed by a time delay of seconds, minutes, hours or days and before radiation treatment. The combined modality treatment also incorporates administration of the radiation treatment followed by the adenoviral treatment, including but not necessarily requiring a time interval between radiation treatment and delivery of the adenovirus, of seconds, minutes, hours or days.

Assessment of the efficacy of a particular treatment regimen may be determined by any of the techniques known in the art, including diagnostic methods such as imaging techniques, analysis of serum tumor markers, biopsy, the presence, absence or amelioration of tumor associated symptoms. It will be understood that a given treatment regime may be modified, as appropriate, to maximize efficacy.

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g., amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

All publications and patent applications cited in this specification are herein incorporated by reference as if each individual publication or patent application were specifically and individually indicated to be incorporated by reference.

The present invention has been described in terms of particular embodiments found or proposed by the present inventor to comprise preferred modes for the practice of the invention. It will be appreciated by those of skill in the art that, in light of the present disclosure, numerous modifications and changes can be made in the particular embodiments exemplified without departing from the intended scope of the invention. For example, due to codon redundancy, changes can be made in the underlying DNA sequence without affecting the protein sequence. Moreover, due to biological functional equivalency considerations, changes can be made in protein structure without affecting the biological action in kind or amount. All such modifications are intended to be included within the scope of the appended claims.

EXPERIMENTAL

EXAMPLE 1

Based on the fact that human melanoma has tumor-specific makers that share significant homology with their murine counterparts, the transcription control elements from a number of melanoma-specific biomarkers have been identified, isolated and applied to oncolytic adenoviruses specific for human melanoma. ARCA (Attenuated Replication Competent Adenovirus) is a technology to build recombinant adenoviruses specific for cancer by restricting virus replication to only cancer cells. After infection of melanoma cells, the melanoma specific transcriptional control mechanism turns on ARCA replication, and the virus can then replicate and lyse the cancer cells. The transcription control elements of the melanoma specific biomarkers are the key elements in composing the melanoma specific adenovirus. We have isolated different melanoma-specific elements from the human and mouse genomes and applied in ARCAs for melanoma treatment. For example, the CV859 vector has an E1A-TRE derived from tyrosinase, E1B under control of an IRES with no independent promoter. The E1A promoter is absent, the E1A enhancer is present and E3 is expressed.

Construction of a Replication-Competent Adenovirus Vector with a Tyrosinase TRE and EMCV IRES. CP621 is a plasmid containing a human tyrosinase enhancer and promoter elements in a PinAI fragment. This fragment is ligated to the PinAI site on CP627 to generate CP1078. CP1078 is combined with pBHGE3 to generate a new melanoma specific virus, CV859. SEQ ID NO:1 depicts the polynucleotide sequence of the PinAI fragment which contains a tyrosinase promoter and enhancer.

EXAMPLE 2

In Vitro Characterization of Melanocyte-Specific TRE-Containing Adenoviral Constructs An especially useful objective in the development of melanocyte cell-specific adenoviral vectors is to treat patients with melanoma. Methods are described below for measuring the activity of a melanocyte-specific TRE and thus for determining whether a given cell allows a melanocyte-specific TRE to function.

Cells and Culture Methods

Host cells such as HepG2 (liver); Lovo (colon); LNCaP (prostate); PMEL (melanoma); SKMel (melanoma); G361 (melanoma) and MeWo cells are obtained at passage 9 from the American Type Culture Collection (Rockville, Md.). MeWo cells are maintained in RPMI 1640 medium (RPMI) supplemented with 10% fetal bovine serum (FBS; Intergen Corp.), 100 units/mL of penicillin, and 100 units/mL streptomycin. MeWo cells being assayed for luciferase expression are maintained in 10% strip-serum (charcoal/dextran treated fetal bovine serum to remove T3, T4, and steroids; Gemini Bioproduct, Inc., Calabasas, Calif.) RPMI.

Transfections of MeWo Cells For transfections, MeWo cells are plated out at a cell density of $5 \times 10^5$ cells per 6-cm culture dish (Falcon, N.J.) in complete RPMI. DNAs are introduced into MeWo cells after being complexed with a 1:1 molar lipid mixture of N-[1-(2,3-dioleyloxy)propyl-N, N,N-trimethylammonium chloride (DOTAP™; Avanti Polar Lipids, AL) and dioleoyl-phosphatidylethanolamine (DOPE™; Avanti Polar Lipids, AL); DNA/lipid complexes are prepared in serum-free RPMI at a 2:1 molar ratio. Typically, 8 µg (24.2 nmole) of DNA is diluted into 200 µL of incomplete RPMI and added dropwise to 50 nmole of transfecting, lipids in 200 µL of RPMI with gentle vortexing to insure homogenous mixing of components. The DNA/lipid complexes are allowed to anneal at room temperature for 15 minutes prior to their addition to MeWo cells. Medium is removed from MeWo cells and replaced with 1 mL of serum-free RPMI followed by the dropwise addition of DNA/lipid complexes. Cells are incubated with complexes for 4–5 hours at 37° C., 5% $CO_2$. Medium was removed and cells washed once with PBS. The cells were then trypsinized and resuspended in 10% strip-serum RPMI (phenol red free). Cells were replated into an opaque 96-well tissue culture plate (Falcon, N.J.) at a cell density of 40,000 cells/well per 100 µL media and assayed.

Virus Yield assays. To determine whether the adenoviral constructs described above replicate preferentially in melanocytes, plaque assays are performed. Plaquing efficiency is evaluated in the following cell types: melanoma cells (MeWo), prostate tumor cell lines (LNCaP), breast normal cell line (HBL-100), ovarian tumor cell line (OVCAR-3, SK-OV-3), and human embryonic kidney cells (293). 293 cells serve as a positive control for plaquing efficiency, since this cell line expresses Ad5 EIA and EIB proteins. For analyzing constructs comprising a melanocyte-specific TRE, cells that allow a melanocyte-specific TRE to function, such as the cell lines provided above and cells that do not allow such function, such as HuH7, HeLa, PA-1, or G361, are used. The plaque assay is performed as follows: Confluent cell monolayers are seeded in 6-well dishes eighteen hours before infection. The monolayers are infected with 10-fold serial dilutions of each virus. After infecting monolayers for four hours in serum-free media (MEM), the medium is removed and replaced with a solution of 0.75% low melting point agarose and tissue culture media. Plaques are scored two weeks after infection.

EXAMPLE 3

In order to develop ARCA products against human melanoma, several melanoma-specific transcriptional regulatory elements (TREs) were cloned and applied in building a series of DNA constructs. The primary platform for using the TREs was by use of a single TRE to control the E1A-IRES-E1B bicistronic cassette. Alternatively, different TREs were used to control E1A and E1B separately. The following provide a description of the structure of the TREs and the derived constructs used in generating ARCAs for treatment of melanoma. Schematics of the constructs are provided in FIG. 1.

Human melanoma-specific TREs. Human melanoma studies have shown good melanoma-specific antigens or markers including tyrosinase, TRP-1 (tyrosinase related protein 1), TRP-2, enzymes involved in melanin biosynthesis, MART-1/melan-A (Melanoma Antigen Recognized by cytolytic T cells-1), MAGE-1 and BAGE-1. Some of these human products have murine counterparts with significant homology, not only within their coding sequences, but also within their TREs. Therefore, TREs were cloned from human or murine genomic DNA by PCR, and used as human melanoma-specific TREs. All the indicated enzyme sites were introduced for cloning purpose.

The murine tyrosinase enhancer element (mTyr-E) was PCR amplified from mouse genomic DNA by primer set: 5'-CGGCCGCAAGGTCATAGTTCCTGCCAGC (SEQ ID NO:2) and =5'-TACTCGAGTATTGTGGTTTGCCAG-GACCC (SEQ ID NO:3). The mTyr-E sequence is provided as SEQ ID NO:4, which is annotated to indicate an EagI site at the 5' end and an XhoI site at the 3' end, with the restriction sites added for cloning purposes.

The murine tyrosinase promoter (mTyr-P) was PCR amplified from the mouse genomic DNA with the primer set 5'-CGGCCGTGTCACAGACTTCTTTTCC (SEQ ID NO:5) and 5'-TACTCGAGGAATCTAGATGTTTCAT-GACC (SEQ ID NO:6). The mTyr-P sequence is provided as SEQ ID NO:7, which is annotated to indicate an XhoI site at the 5' end and an EagI site at the 3' end, with the restriction sites added for cloning purposes.

To build a murine tyrosinase enhancer/promoter (mTyr-EP or mTyr-EEP) structure, the mTyr-P PCR product was first cloned into pBluscript via XhoI and EagI to generate CP1050. The mTyr-E PCR product was cloned into pBluescript via XhoI and EagI sites to get CP1051. A KpnI-EagI fragment from CP1050 was cloned into KpnI and EagI sites of CP1051 to generate CP1054, which has one copy of mTyr-E proceeding mTyr-P. A PCR product from CP1054 with primer set 5'-AAATACCGGTCA AGGTCATAGTTC-CTGCCAGC (SEQ ID NO:8) and 5'-AAATACCGGT-GAGTGTCA CAGACTTCTTTTCC (SEQ ID NO:9) gives a DNA fragment containing mTyr-EP with two AgeI sites at the ends.

mTyr-EEP was constructed by first PCR amplifying the CP1051 with primer set 5'-ACTCGAGAAGGTCATAGT-TCCTGCCAGC (SEQ ID NO:10) and 5'-ACTCGAGTAT-TGTGGTTTGCCAGGACCC (SEQ ID NO:11) to introduce the XhoI sites to the ends of mTyr-E. The XhoI fragment containing the mTyr-E was cloned to the XhoI site of CP1054 to get CP1056, which has two copies of mTyr-E and one mTyr-P. After putting a pair of AgeI linkers at SnaBI and SmaI sites, the mTyr-EEP structure was contained in a 0.9 Kb AgeI fragment.

The human tyrosinase enhancer (hTyr-EP) was cloned from human genomic DNA by PCR with primer set 5'-AAC-CGGTTGAAAATGATAAGTTGAATTCTGTCTTC (SEQ ID NO:12) and 5'-ACTCGAGTGAAGAGGAA-GAGAAGTTTCCATG (SEQ ID NO:13), which has AgeI and XhoI sites at 5' and 3' ends respectively. The promoter element (hTyr-P) was cloned by PCR with primer set 5'-ACTCGAGATTACTAACCTTATTGT-TAATATTCTAACC (SEQ ID NO:14) and 5'-AACCGGT-CACAAGGTCTGCAGGAACTGGC (SEQ ID NO:15), which have XhoI and AgeI sites at the 5' and 3' ends respectively. The enhancer and the promoter fragment were linked via an XhoI site to get the hTyr-EP structure set forth in SEQ ID NO:16 (with introduced flanking AgeI sites at both ends).

The Human Melanoma Antigen Recognized by cytolytic T cells-1 promoter (hMart-P) was PCR amplified from human genomic DNA using primer set 5'-AAATACCGGT-CAAAAGTAATTGTGGTGTCGGACC (SEQ ID NO:17) and 5'-AAATACCGGTAGTCCTCTGTCTGCTGGCTGG (SEQ ID NO:18). The PCR product (set forth as SEQ ID NO:19 and showing the introduced AgeI sites) was used as the hMart promoter.

DNA Constructs for Generating Human Melanoma-Specific ARCAs

A single TRE was used to control an E1A-IRES-E1B bicistronic cassette, in order to reach higher tumor specificity. Using the cloned melanoma-specific TREs described above, a series DNA constructs were developed based on this platform. In one exemplary study, CP686, which contains both the E1A and E1B genes under control of an alpha fetoprotein (AFP) TRE, was used as the E1 region DNA platform (previously described in Cancer Res. 2001, 61:517). For construct CP1043, an AgeI fragment which contains AFP element was replaced with the hMart promoter, also an AgeI fragment. Similar cloning strategies were applied for CP1145 and CP1147 construction by replacing the corresponding AgeI fragments, mTyr-EP or mTyr-EEP, to the AFP fragment on CP686.

As an alternative way to control both E1A and E1B, different TREs were used to control E1A and E1B separately. To construct CP1150, the hTyr-P PCR product, a 0.5 Kb AgeI fragment, was cloned into AgeI site of CP124 (previously described in Cancer Res. 1999, 59:4200). Another hMart-P fragment with flanking EagI sites was cloned into the EagI site and to get CP1150. This hMart-P fragment was taken from CP1015, a plasmid containing the hMart PCR amplified with primer set 5'-CGGCCG-CAAAAGTAATTGTGGTGTCGGACC (SEQ ID NO:20) and 5'-ATTCTAGAAGTCCTCTGTCTGCTGGCTGG (SEQ ID NO:21) and cloned by pBluescript via HincII and XbaI sites. From CP1150, the hTyr-P can be replaced by mTyr-EP or mTyr-EEP via their AgeI sites to obtain CP1148 or CP1149.

In one embodiment the adenovirus vectors of the invention are considered to be "armed". An "armed" adenovirus comprises a therapeutic gene within the genome of the adenovirus. Exemplary therapeutic genes include those that encode an enzyme which converts an inactive prodrug molecule into an active chemotherapeutic agent and transgenes that facilitate killing of cancer cells by the immune system, e.g., granulocyte macrophage colony stimulating factor (GM-CSF), interleukin-2 (IL-2) and tumor necrosis factor (TNF).

Armed ARCAs with melanoma-TREs were prepared as a means to increase the potency of melanoma-specific ARCAs. In general, therapeutic genes are delivered with the melanoma-specific ARCAs or the viral genome is modified to reach higher potency. For example, in CP686, the E1B region has both E1B 19K and 55K coding sequences. However, in CP1199 the E1B 19K sequence was deleted and the same modification may be applied in other DNA constructs for melanoma ARCAs. Furthermore, the expression of cytokines such as human GM-CSF or IL-2 etc. is achieved by incorporating foreign genes into the ARCAs. Therapeutic gene incorporation at various sites in the ARCAs genome is possible, in particular in the E3 region. The use of different therapeutic genes at different locations on the viral genome is effective to generate improved ARCA products.

Figure 2:
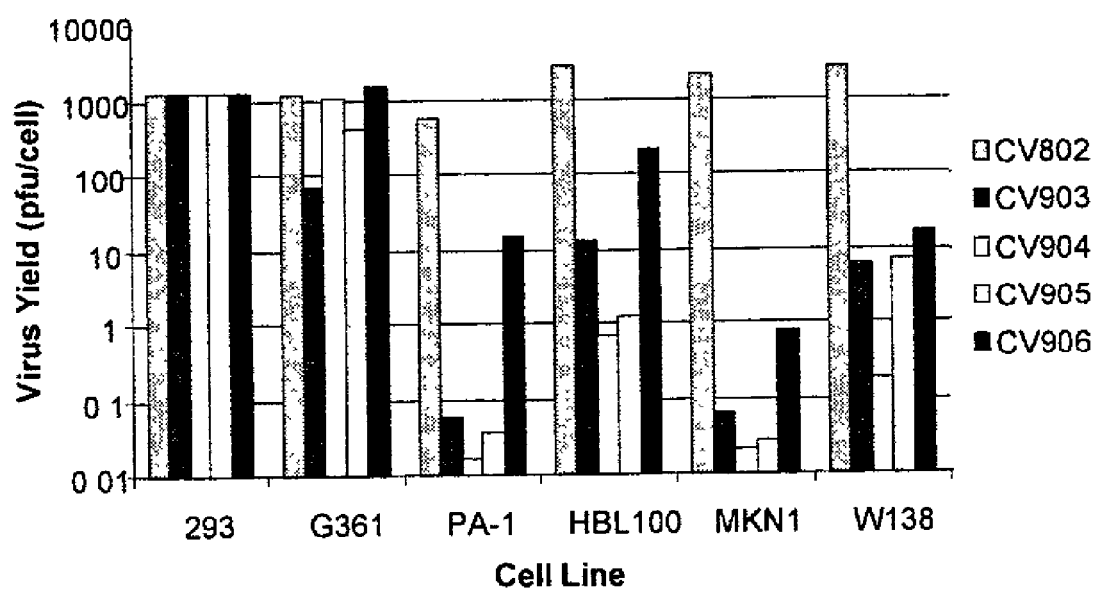
FIG. 2 is a comparison of melanoma-specific virus replication in selected cell lines.

The structures of the melanoma-specific viruses shown in FIG. 1 were PCR verified. After preliminary characterization by virus yield assay, CV904 was selected for further characterization (FIG. 2). In FIG. 2, CV904 appears to have the best melanoma-specific profile, where the difference in virus yield between a melanoma cell line (G361) and other non-melanoma cell lines is about 1000 to 50000 fold.

Figure 3:
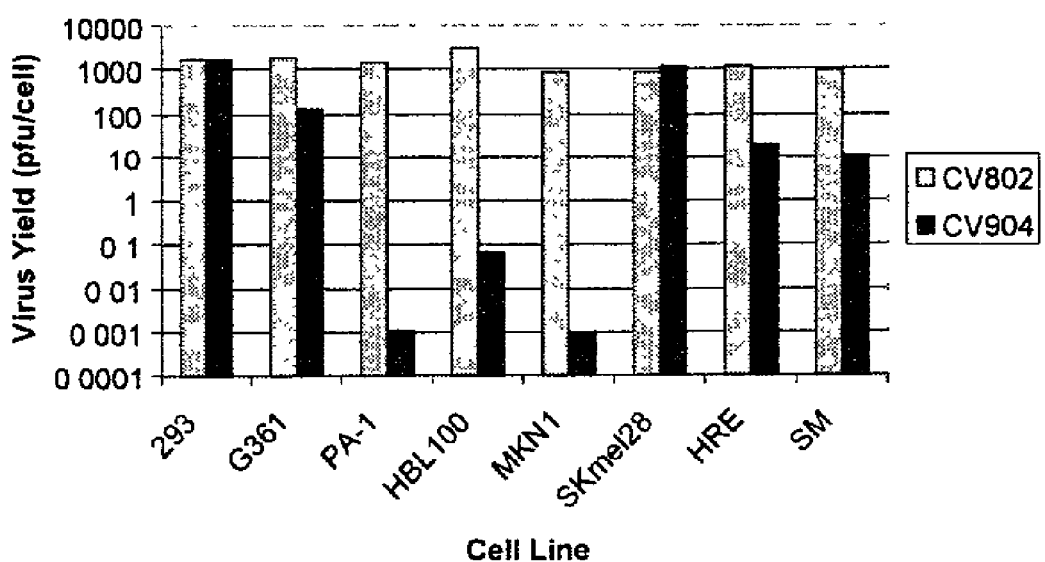
FIG. 3. is a comparison of melanoma-specific virus replication of the melanoma-specific adenovirus, CV904, to a wild type adenovirus (CV802), in selected cell lines.

To further verify the replication selectivity, CV904 was tested on more cell lines including Skmel28, another melanoma cell line; HRE and SM, two human primary cell lines (FIG. 3). CV904 showed good replication in both melanoma cells as compared to the wild type virus control, whereas on other cells, it exhibited significant attenuation, suggesting a cancer-selective profile.

Figure 4:
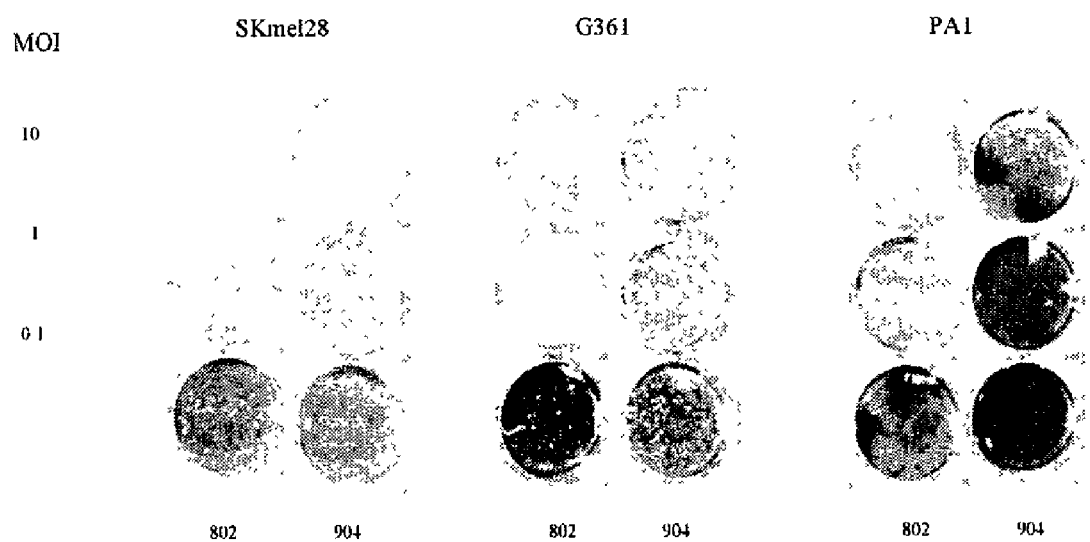
FIG. 4. depicts the cytopathic effect of CV904 and CV802 on different cells: Skmel28 (melanoma cell line; 4A), G361 (melanoma cell line; 4B) and PA1 (an ovarian cancer cell line; 4C).
Figure 5:
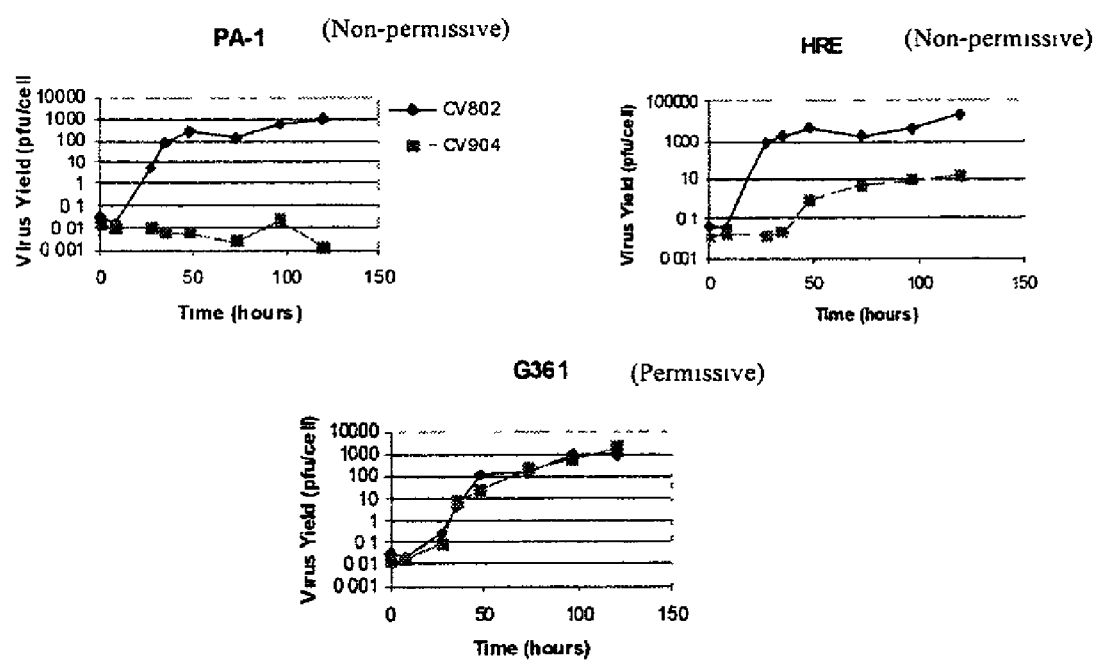
FIG. 5. depicts growth curves of CV904 on different cells: Skmel28 (a melanoma cell line; 5A), HRE (human primary non-melanoma cells; 5B), and G361 (a melanoma cell line; 5C).

The cancer-selective profile of CV904 was also demonstrated in other types of studies as shown in FIG. 4 and FIG. 5. In FIG. 4, CV904 exhibited a clear cytotoxic effect on both melanoma cells similar to the killing exhibited by wild type (wt) adenovirus CV802, whereas on PA1 cells, only wt virus killed the cells. In virus growth curves (FIG. 5), both CV904 and CV802 show a similar growth pattern on melanoma cells, however, a dramatic attenuation of CV904 can be found in other cell lines as compared to CV802.

From the comparison of CV904 and other melanoma viruses, it is clear that the melanoma adenoviruses of the invention have a good cancer-selective profile and can be specifically targeted to melanoma cells.

What is claimed is:

1. A replication-competent adenovirus vector for selective cytolysis of a melanoma target cell comprising an adenovirus gene essential for replication, under transcriptional control of a first melanoma cell specific transcriptional regulatory element (TRE) derived from the 5' region of a gene, said TRE being selected from the group consisting of a tyrosinase TRE sequence presented as SEQ ID NO: 4, SEQ ID NO: 7, and SEQ ID NO: 16.

2. The adenovirus vector according to claim 1, wherein said first melanoma cell specific TRE comprises the tyrosinase TRE sequence presented as SEQ ID NO: 4.

3. The adenovirus vector according to claim 1, wherein said first melanoma cell specific TRE comprises the tyrosinase TRE sequence presented as SEQ ID NO: 7.

4. The adenovirus vector according to claim 1, wherein said first melanoma cell-specific TRE comprises the tyrosinase TRE sequence presented as SEQ ID NO: 16.

5. The adenovirus vector of claim 1, wherein said first melanoma cell specific TRE comprises two or more enhancers.

6. The adenovirus vector of claim 1, wherein the adenoviral vector comprises co-transcribed first and second adenoviral genes under transcriptional control of said first melanoma cell-specific TRE wherein the second gene is under translational control of an IRES.

7. The adenovirus vector of claim 1, wherein said adenoviral gene essential for replication is an early gene.

8. The adenovirus vector of claim 1, wherein said adenoviral gene essential for replication is a late gene.

9. The adenovirus vector of claim 7, wherein said adenoviral gene essential for replication is E1A or E1B.

10. The adenovirus vector of claim 7, wherein E1A or E1B has a mutation in or deletion of its endogenous promoter.

11. The adenovirus vector of claim 10, wherein E1B has a deletion of the 19-kDa region.

12. A composition comprising:
the replication-competent adenovirus vector according to claim 1; and a pharmaceutically acceptable excipient.

13. An isolated host cell comprising the adenovirus vector of claim 1.

14. A method for suppressing melanoma tumor growth in an individual, the method comprising:
administering to the individual the melanoma cell-specific adenovirus vector according to claim 1.

15. A replication competent adenovirus vector according to claim 1; wherein the difference in yield of said adenovirus between a melanoma cell and non-melanoma cell is at least about 1000 fold following infection of said melanoma cell.

16. The replication competent adenovirus vector of claim 15, wherein the adenoviral vector comprises co-transcribed first and second adenoviral genes under transcriptional control of said melanoma cell-specific TRE wherein the second gene is under transcriptional control of an IRES.

17. The replication competent adenovirus vector of claim 15, wherein said melanoma cell specific transcriptional regulatory element (TRE) comprises SEQ ID NO: 16.

18. The replication competent adenovirus vector of claim 15, wherein said melanoma cell specific transcriptional regulatory element (TRE) comprises SEQ ID NO: 7.

19. The replication competent adenovirus vector of claim 15, wherein said melanoma cell specific transcriptional regulatory element (TRE) comprises SEQ ID NO: 4.

* * * * *